(12) United States Patent
Glass et al.

(10) Patent No.: US 10,576,076 B2
(45) Date of Patent: Mar. 3, 2020

(54) PHARMACEUTICAL COMBINATION OF EVEROLIMUS WITH DACTOLISIB

(71) Applicants: David Glass, Cambridge, MA (US); Joan Mannick, Cambridge, MA (US); Leon Murphy, Cambridge, MA (US)

(72) Inventors: David Glass, Cambridge, MA (US); Joan Mannick, Cambridge, MA (US); Leon Murphy, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/575,703

(22) PCT Filed: May 20, 2016

(86) PCT No.: PCT/IB2016/052980
§ 371 (c)(1),
(2) Date: Nov. 20, 2017

(87) PCT Pub. No.: WO2016/185443
PCT Pub. Date: Nov. 24, 2016

(65) Prior Publication Data
US 2018/0289694 A1 Oct. 11, 2018

Related U.S. Application Data

(60) Provisional application No. 62/164,354, filed on May 20, 2015.

(51) Int. Cl.
*A61K 31/4745* (2006.01)
*A61K 31/436* (2006.01)

(52) U.S. Cl.
CPC ........ *A61K 31/4745* (2013.01); *A61K 31/436* (2013.01)

(58) Field of Classification Search
CPC .................. A61K 31/4745; A61K 31/436
See application file for complete search history.

(56) References Cited

U.S. PATENT DOCUMENTS 3,929,992 A 12/1975 Sehgal et al.
5,665,772 A 9/1997 Cottens et al.
(Continued)

FOREIGN PATENT DOCUMENTS

CN 1195289 A 10/1998
CN 101862297 A 10/2010
(Continued)

OTHER PUBLICATIONS

Araki et al., "The role of mTOR in memory of CD8+ T-cell differentiation," Immunol Rev., 235(1):234-243 (2010).
(Continued)

*Primary Examiner* — San Ming R Hui
(74) *Attorney, Agent, or Firm* — Andrea L. C. Reid; Dechert LLP

(57) ABSTRACT

The present invention relates to a combination comprising (a) RAD001, or a pharmaceutically acceptable salt thereof, and (b) BEZ235, or pharmaceutically acceptable salt thereof, for simultaneous, separate or sequential use for enhancement of an immune response; a pharmaceutical composition comprising such combination; a method of enhancing immune response in a subject comprising administration of said combination to a subject in need thereof; use of such combination for preparation of a medicament for the enhancement of an immune response; and a commercial package thereto.

21 Claims, 9 Drawing Sheets

Rationale for RAD+BEZ combination therapy: Synergistic inhibition of both S6K and 36K and 4EBP1

(56) References Cited

U.S. PATENT DOCUMENTS

| | | |
|---|---|---|
| 5,741,677 A | 4/1998 | Kozlowski et al. |
| 6,015,815 A | 1/2000 | Mollison |
| 6,440,458 B1 | 8/2002 | Yamashita et al. |
| 7,091,213 B2 | 8/2006 | Metcalf, III et al. |
| 7,667,039 B2 | 2/2010 | Garcia-Echeverria et al. |
| 7,994,170 B2 | 8/2011 | Garcia-Echeverria et al. |
| 8,431,592 B2 | 4/2013 | Garcia-Echeverria et al. |
| 8,436,177 B2 | 5/2013 | Stowasser et al. |
| RE44,768 E | 2/2014 | Skotnicki et al. |
| 9,358,229 B2 | 6/2016 | Vannucchi et al. |
| 9,358,236 B2 | 6/2016 | Murphy et al. |
| 9,370,508 B2 | 6/2016 | Garcia-Echeverria et al. |
| 10,004,803 B2 | 6/2018 | Mannick et al. |
| 2004/0228917 A1 | 11/2004 | Oshlack et al. |
| 2005/0101624 A1 | 5/2005 | Betts et al. |
| 2006/0264453 A1 | 11/2006 | Mudumba et al. |
| 2007/0036857 A1 | 2/2007 | Becker |
| 2007/0265294 A1 | 11/2007 | Kleinman |
| 2008/0194579 A1 | 8/2008 | Garcia-Echerverria et al. |
| 2008/0206322 A1 | 8/2008 | Becker |
| 2009/0082387 A1 | 3/2009 | Czarnik |
| 2009/0088373 A1 | 4/2009 | Gallo et al. |
| 2009/0270515 A1 | 10/2009 | Gruber |
| 2010/0056558 A1 | 3/2010 | Garcia-Echerverria et al. |
| 2010/0105696 A1 | 4/2010 | Garcia-Echerverria et al. |
| 2010/0129357 A1 | 5/2010 | Garcia-Martinez |
| 2010/0150829 A1 | 6/2010 | Garcia-Martinez |
| 2010/0152147 A1 | 6/2010 | Fugue et al. |
| 2010/0168153 A1 | 7/2010 | Stowasser et al. |
| 2010/0196311 A1 | 8/2010 | Kim et al. |
| 2010/0196365 A1 | 8/2010 | Garcia-Echeverria et al. |
| 2010/0233733 A1 | 9/2010 | Fantl |
| 2010/0260858 A1 | 10/2010 | Ruddy |
| 2011/0020338 A1 | 1/2011 | Garcia-Echeverria et al. |
| 2011/0129496 A1 | 6/2011 | Ahmed et al. |
| 2011/0230476 A1 | 9/2011 | Niu et al. |
| 2011/0251202 A1 | 10/2011 | Garcia-Echerverria et al. |
| 2012/0148552 A1 | 6/2012 | Jensen |
| 2012/0207751 A1 | 8/2012 | Garcia-Echeverria et al. |
| 2012/0282252 A1 | 11/2012 | Garcia-Echeverria et al. |
| 2013/0178479 A1 | 7/2013 | Chen et al. |
| 2013/0245061 A1 | 9/2013 | Cao et al. |
| 2013/0289064 A1 | 10/2013 | Stowasser et al. |
| 2013/0296316 A1 | 11/2013 | Pollastri et al. |
| 2013/0309258 A1 | 11/2013 | June |
| 2014/0206678 A1 | 7/2014 | Shenk et al. |
| 2014/0242162 A1 | 8/2014 | Diederich et al. |
| 2014/0243396 A1 | 8/2014 | Griffin et al. |
| 2015/0000744 A1 | 1/2015 | Park et al. |
| 2015/0051266 A1 | 2/2015 | Kochenderter |
| 2015/0079155 A1 | 3/2015 | Jensen |
| 2015/0140036 A1 | 5/2015 | Mannick et al. |
| 2015/0157645 A1 | 6/2015 | Hirawat et al. |
| 2016/0045441 A1 | 2/2016 | Diederich et al. |
| 2016/0046724 A1 | 2/2016 | Brogdon |
| 2016/0051651 A1 | 2/2016 | Brogdon |
| 2016/0068601 A1 | 3/2016 | Brogdon |
| 2016/0096892 A1 | 4/2016 | Brogdon |
| 2017/0049754 A1 | 2/2017 | Diederich et al. |
| 2017/0274014 A1 | 9/2017 | Brogdon et al. |
| 2017/0281753 A1 | 10/2017 | Mannick et al. |
| 2018/0161280 A1 | 6/2018 | Diederich et al. |

FOREIGN PATENT DOCUMENTS

| | | | |
|---|---|---|---|
| CN | 101969931 A | 2/2011 | |
| CN | 102138903 A | 8/2011 | |
| CN | 102199152 | 9/2011 | |
| CN | 102292078 A | 12/2011 | |
| DE | 2347682 | 4/1974 | |
| EP | 0868911 | 10/1998 | |
| JP | H11509223 | 8/1999 | |
| JP | 2003530340 | 10/2003 | |
| JP | 2004035547 | 2/2004 | |
| JP | 2004354394 A | 12/2004 | |
| JP | 2006188539 A | 7/2006 | |
| JP | 2009102341 | 5/2009 | |
| TW | 550091 B | 9/2003 | |
| WO | 9409010 | 4/1994 | |
| WO | 9514023 | 5/1995 | |
| WO | 9516691 | 6/1995 | |
| WO | 9641807 | 12/1996 | |
| WO | 9802441 | 1/1998 | |
| WO | 9915530 | 4/1999 | |
| WO | 0114387 | 3/2001 | |
| WO | 2005034916 A1 | 4/2005 | |
| WO | 2006094507 | 9/2006 | |
| WO | 2006112806 A2 | 11/2006 | |
| WO | 2006122806 | 11/2006 | |
| WO | 2008016633 A2 | 2/2008 | |
| WO | 2008064093 | 5/2008 | |
| WO | 2008103636 | 8/2008 | |
| WO | 2008103636 A1 | 8/2008 | |
| WO | 2009013305 A1 | 1/2009 | |
| WO | 2009118324 | 10/2009 | |
| WO | 2009118324 A1 | 10/2009 | |
| WO | 2010056754 A2 | 5/2010 | |
| WO | 2010049481 A1 | 6/2010 | |
| WO | 2010118419 A2 | 10/2010 | |
| WO | 2010129622 A1 | 11/2010 | |
| WO | 2011031896 A2 | 3/2011 | |
| WO | 2012006619 A2 | 1/2012 | |
| WO | 2012047775 A1 | 4/2012 | |
| WO | 2012075253 A2 | 6/2012 | |
| WO | 2012103524 A2 | 8/2012 | |
| WO | 2012110953 A1 | 8/2012 | |
| WO | WO-2012110953 A1 * | 8/2012 | ........... A61K 31/436 |
| WO | 2013023119 A1 | 2/2013 | |
| WO | 2013049300 A1 | 4/2013 | |
| WO | 2013050419 A1 | 4/2013 | |
| WO | 2013184621 A2 | 12/2013 | |
| WO | 2014137946 A1 | 9/2014 | |
| WO | 2014147567 | 9/2014 | |
| WO | 2014191128 A1 | 12/2014 | |
| WO | 2015073644 A1 | 5/2015 | |
| WO | 2015188119 | 12/2015 | |
| WO | 2016014530 A1 | 1/2016 | |
| WO | 2016064683 A1 | 4/2016 | |
| WO | 2016079332 A1 | 5/2016 | |
| WO | 2016185443 | 11/2016 | |

OTHER PUBLICATIONS

Ballou et al., "Rapamycin and mTOR kinase inhibitors," J Chem Biol., Nov. 2008, vol. 1(1-4), pp. 27-36. doi: 10.1007/s12154-008-0003-5. Epub May 15, 2008.

Bitto et al., "Transient rapamycin treatment can increase lifespan and healthspan in middle-aged mice," Elife, Aug. 23, 2016, 5:e16351. doi: 10.7554/eLife.16351.

Clegg et al., "Frailty in elderly people," Lancet, Mar. 2, 2013, vol. 381, No. 9868, pp. 752-762. doi: 10.1016/S0140-6736(12)62167-9. Epub Feb. 8, 2013. Review. Erratum in: Lancet. Oct. 19, 2013;382(9901):1328.

Dello Russo et al., "Involvement of mTOR kinase in cytokine-dependent microglial activation and cell proliferation," Biochemical Pharmacology, 2009, vol. 78, No. 9, pp. 1242-1251.

Dominick et al., "Regulation of mTOR activity in Snell dwarf and GH receptor gene-disrupted mice," Endocrinology, Feb. 2015, vol. 156, No. 2, pp. 565-575. doi: 10.1210/en.2014-1690. Epub Dec. 2, 2014.

Feldman et al., "Active-site inhibitors of mTOR target rapamycin-resistant outputs of mTORC1 and mTORC2," PLoS Biol., Feb. 10, 2009, vol. 7, No. 2, p. e38 (13 pages).

Golden-Mason et al., "Upregulation of PD-1 Expression on Circulating and Intrahepatic Hepatitis C Virus-Specific CD8+ T Cells Associated with Reversible Immune Dysfunction," Journal of Virology, Sep. 2007, vol. 81, No. 17, pp. 9249-9258.

Harari et al., "A robust type I interferon gene signature from blood RNA defines quantitative but not qualitative differences between three major IFNβ drugs in the treatment of multiple sclerosis," Hum Mol Genet., Jun. 1, 2015, vol. 24, No. 11, pp. 3192-3205. doi: 10.1093/hmg/ddv071.

(56) References Cited

OTHER PUBLICATIONS

Huye et al., "Combining mTor inhibitors with rapamycin-resistant T cells: a two-pronged approach to tumor elimination," Mol Ther., Dec. 2011, vol. 19, No. 12, pp. 2239-2248. Epub Aug. 30, 2011.
International Search Report and Written Opinion dated Jun. 13, 2012 in connection with International Application No. PCT/IB2012/050669.
International Search Report and Written Opinion dated Dec. 10, 2012 in connection with International Application No. PCT/EP2012/069541.
International Search Report and Written Opinion dated Jun. 23, 2014 in connection with Application No. PCT/IB2014/059965.
International Search Report and Written Opinion dated May 6, 2015 in connection with Application No. PCT/US2014/065408.
International Search Report and Written Opinion dated Sep. 16, 2016 in connection with Application No. PCT/IB2016/052980.
IOB et al., "Evidence of increased clinical protection of an MF59-adjuvant influenza vaccine compared to a non-adjuvant vaccine among elderly residents of long-term care facilities in Italy," Epidemiol. Infect., 2005, vol. 133, pp. 687-693.
Keating et al., Nat Immunol. Dec. 2013;14(12):1266-76. Epub Oct. 20, 2013.
Lamming et al., "Depletion of Rictor, an essential protein component of mTORC2, decreases male lifespan," Aging Cell, 2014, vol. 13, pp. 911-7.
Lamming et al., "Rapamycin-induced insulin resistance is mediated by mTORC2 loss and uncoupled from longevity," Science, 2012, vol. 335, pp. 1638-1643.
Laplante et al., "mTOR signaling in growth control and disease," Cell, 2012, vol. 149, pp. 274-293.
Lichterfeld et al., "Telomerase activity of HIV-1-specific CD8+ T cells: constitutive up-regulation in controllers and selective increase by blockade of PD ligand 1 in progressors," Blood, 2008, vol. 112, No. 9, pp. 3679-3687.
Lievesley, Ed., "Ageism and age discrimination in secondary health care in the United Kingdom: A review of the literature," Department of Health, Centre for Policy on Ageing. Dec. 2009.
Mannick et al., "mTOR inhibition improves immune function in the elderly," Science Translational Medicine, Dec. 24, 2014, vol. 6, No. 268, pp. 268ra179.
McMichael et al., "Influenza vaccines: mTOR inhibition surprisingly leads to protection," Nat Immunol., Dec. 2013, vol. 14, No. 12, pp. 1205-1207.
Murray et al., Antivir Chem Chemother., 22(5):205-215 (2012).
Nunes et al., "Expansion of a CD8+PD-1+ Replicative Senescence Phenotype in Early Stage CLL Patients is Associated with Inverted CD4:CD8 Ratios and Disease Progression," Human Cancer Research, 2012, Clinical Cancer Research, vol. 18, No. 3, pp. 678-687.
Nyfeler et al., "RAD001 enhances the potency of BEZ235 to inhibit mTOR signaling and tumor growth," PLoS One, 2012, vol. 7, No. 11, pp. e48548. doi: 10.1371/journal.pone.0048548. Epub Nov. 14, 2012.
Nyfeler et al., "Relieving autophagy and 4EBP1 from rapamycin resistance," Mol Cell Biol., Jul. 2011, vol. 31, No. 14, pp. 2867-2876. doi: 10.1128/MCB.05430-11. Epub May 16, 2011.
Passacantilli et al., "Combined Therapy with RAD001 e BEZ235 overcomes resistance of PET immortalized cell lines to mTOR inhibition," Oncotarget, Jul. 30, 2014, vol. 5, No. 14, pp. 5381-5391.
Pollizzi et al., "Equivalent benefit of mTORCI blockade and combined PI3K-mTOR blockade in a mouse-model of tuberous sclerosis," Molecular Cancer, 2009, vol. 8, No. 38, pp. 1-9.
Sarkar et al., "A rational mechanism for combination treatment of Huntington's disease using lithium and rapamycin," Human Molecular Genetics, 2008, vol. 17, No. 2, pp. 170-178.
Sarkar et al., "Rapamycin and mTOR-independent autophagy inducers ameliorate toxicity of polyglutamine-huntingtin and related proteinopathies." Cell and Death Differentiation, 2009, vol. 16, pp. 46-56.
Serra et al., "NVP-BEZ235, a dual PI3K/mTOR inhibitor, prevents PI3K signaling and inhibits the growth of cancer cells with activating PI3K mutations," Cancer Res., Oct. 1, 2008, vol. 68, No. 19, pp. 8022-8030. doi: 10.1158/0008-5472. CAN-08-1385.
Shimatani et al., "PD-1+ memory phenotype CD4+ T cells expressing C/EBP underlie T cell immunodepression in senescence and leukemia," PNAS, Sep. 15, 2009, vol. 106, No. 37, pp. 15807-15812.
Withers et al., "S6 Kinase and Ageing," Abstract, British Society for Research on Ageing, Annual Scientific Meeting. Sep. 2-4, 2013. University of East Anglia, Norwich.
Zhou et al., "Updates of mTOR inhibitors," Anticancer Agents Med Chem., Sep. 2010, vol. 10, No. 7, pp. 571-581.
U.S. Appl. No. 15/879,272 of Diederich et al., filed Jan. 24, 2018.
U.S. Appl. No. 15/821,229 of Mannick et al., filed Nov. 22, 2017.
U.S. Appl. No. 15/894,683 of Diederich et al., filed Feb. 12, 2018.
International PCT Application No. PCT/IB2017/001579 of Novartis AG, filed Nov. 22, 2017.
Boraschi et al., "The Gracefully Aging Immune System," Sci Transl Med, 2013, vol. 5, No. 185, ps8.
Chen et al., "mTOR regulation and therapeutic rejuvenation of aging hematopoietic stem cells," Sci Signal, 2009, vol. 2, No. 98, ra75.
Ewald et al., "Dauer-independent insulin/IGF-1-signalling implicates collagen remodelling in longevity," Nature, Mar. 5, 2015, vol. 519, No. 7541, pp. 97-101.
Kumar et al., "Age-related decline in immunity: implications for vaccine responsiveness," Expert Rev Vaccines, vol. 7, No. 4, pp. 467-479.
McNab, et al., "Type I interferons in infectious disease," Nat Rev Immunol., Feb. 2015, vol. 15, No. 2, pp. 87-103. doi: 10.1038/nri3787. Review.
Flynn et al., "Late-life rapamycin treatment reverses age-related heart dysfunction," Aging Cell, 2013, vol. 12, pp. 851-862.
International Search Report and Written Opinion dated Mar. 12, 2018 in connection with Application No. PCT/IB2017/001579.
Weinberger et al., "Biology of Immune Responses to Vaccines in Elderly Persons," Clinical Infectious Diseases, vol. 46, pp. 1078-1084 (2008).
Berg et al., "The role of CD8 T cells in innate immunity and in antigen non-specific protection," Current Opinion in Immunology, vol. 18, pp. 338-343 (2006).
Zhang et al., "Aging Leads to Disturbed Homeostasis of Memory Phenotype CD8+ Cells," J. Exp. Med., vol. 195, No. 3, pp. 283-293 (2002).
Cai et al., "Rapamycin, Autophagy, and Alzheimer's Disease," Journal of Biochemical and Pharmacological Research, vol. 1, No. 2, Jun. 2013 (pp. 84-90).
Harrison et al., "Rapamycin fed late in life extends lifespan in genetically heterogeneous mice," Nature, vol. 460, No. 7253, Jul. 2009 (pp. 392-395).
Watanabe et al., "Abstract A167: A phase I study of single-agent BEZ235 (SDS sachet), once- or twice-daily, in Japanese patients with advanced solid tumors," Molecular Cancer Therapeutics, vol. 12, No. 11 Supplemental, Nov. 2013, Abstract (2 pages).
Wilkinson et al., "Rapamycin slows aging in mice," Aging Cell, vol. 11, No. 4, Aug. 2012 (pp. 675-682).

* cited by examiner

Figure1: Rationale for RAD+BEZ combination therapy: Synergistic inhibition of both S6K and 4EBP1
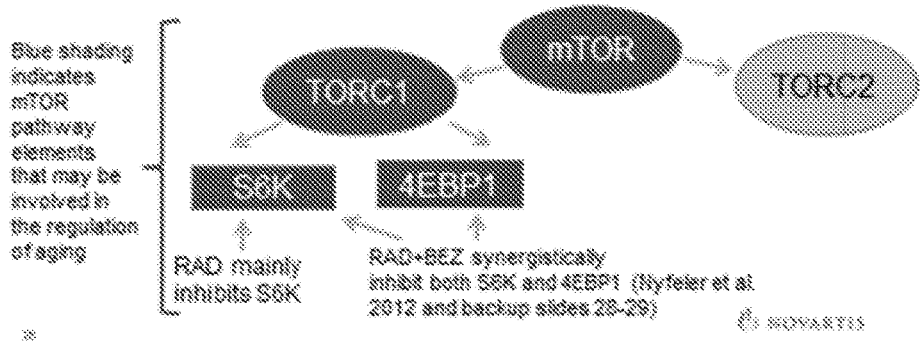

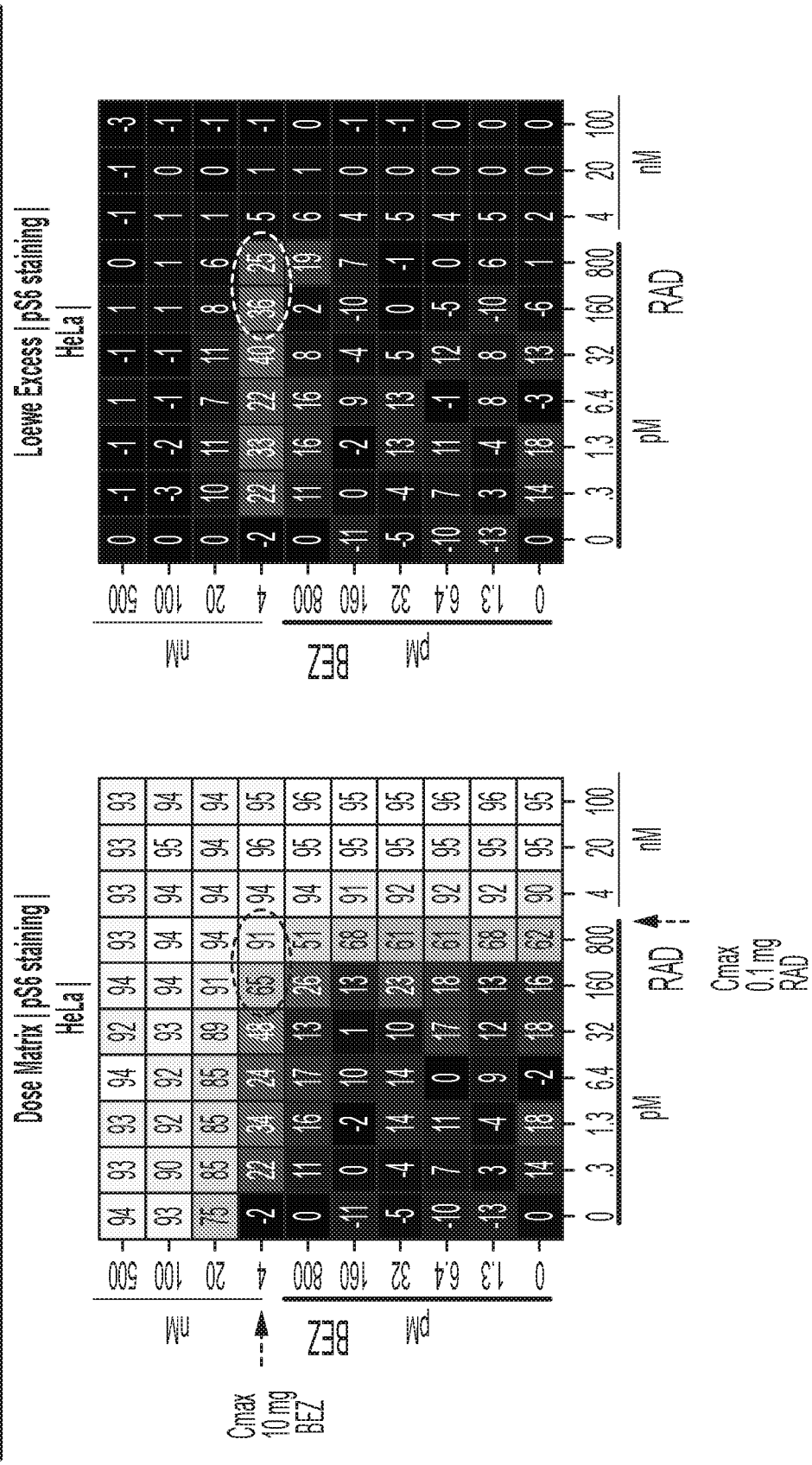

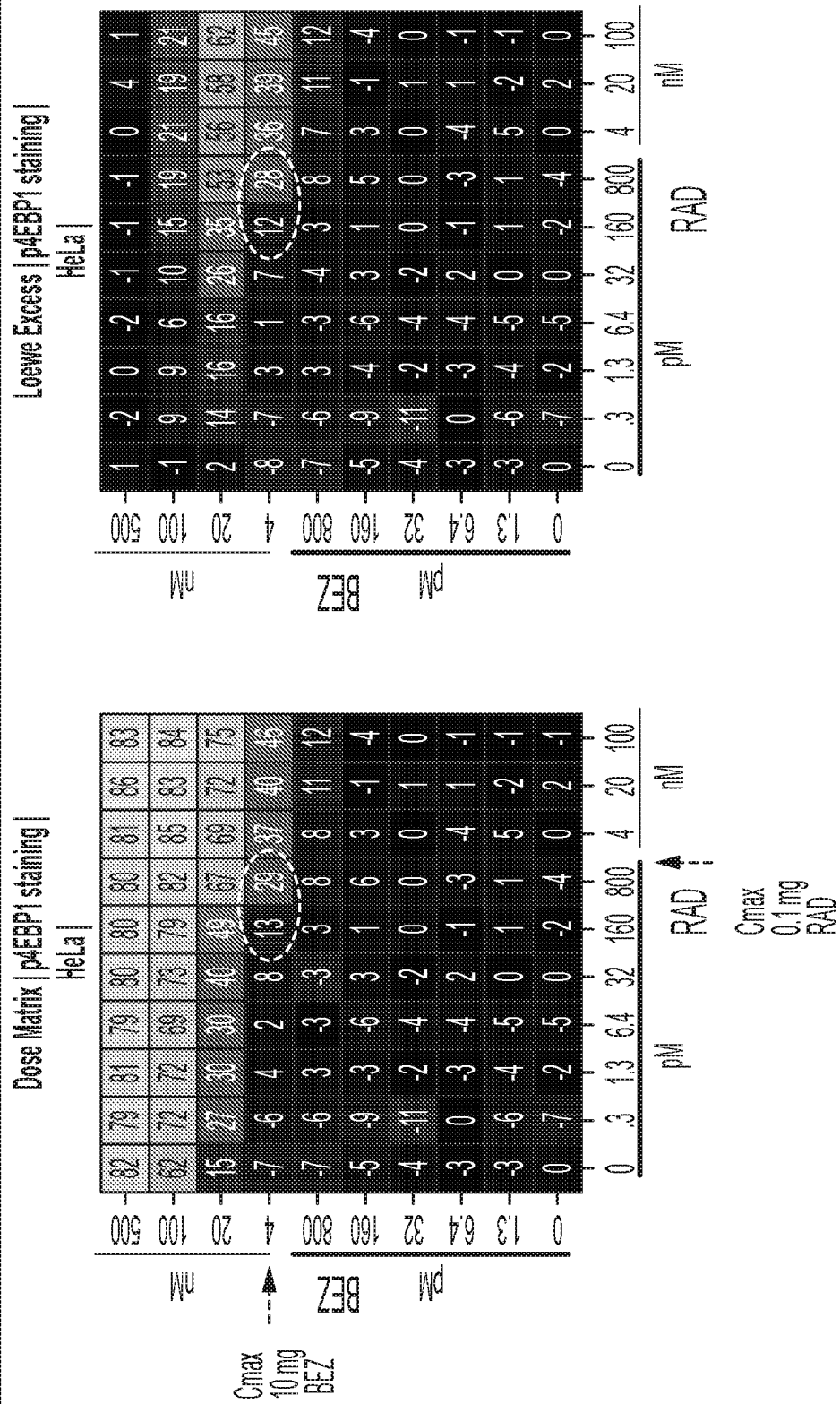

Figure 4: A decline with age in NAD+ levels decreases sirtuin activity resulting in mitochondrial dysfunction, a decline in ATP production and subsequent aging-related organ dysfunction. To determine if mTOR inhibitors increase NAD+ levels and ATP production in old rats, NAD+ and ATP levels were measured in the plasma of old rates treated for 6 weeks with RAD001, BEZ235 or a combination of RAD001 and BEZ235. Only the combination of RAD001 and BEZ235 led to a significant increase in NAD+ and ATP levels.

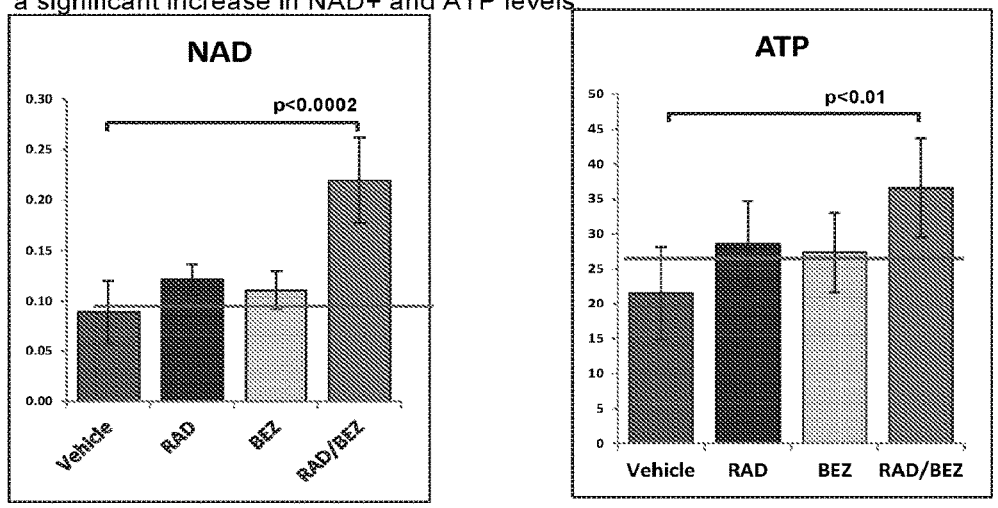

Figure 5: shows that RAD+BEZ increased immune response to all 3 strains of flu by over 20% (a clinically relevant increase) whereas monotherapy met this cut off for only 1 out of 3 strains.
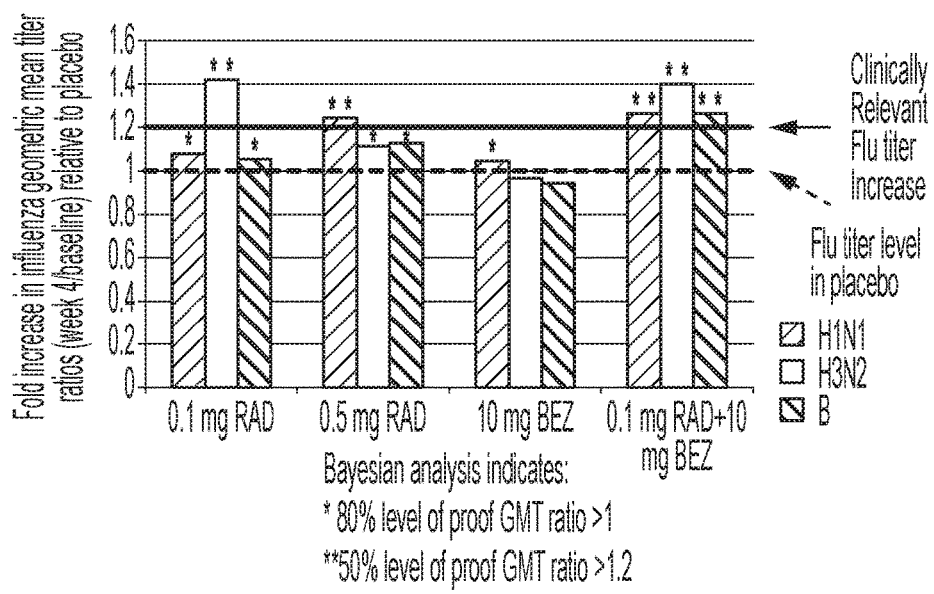

Figure 6: Increase in energy spontaneously reported by subjects predominantly in the everolimus+BEZ235 combination cohort.

Safety Results
*Related adverse events*

|  | Everolimus 0.1 mg N=52 | Everolimus 0.5 mg N=54 | BEZ235 10 mg N=53 | Everolimus 0.1 mg and BEZ235 10 mg N=53 | Placebo, pooled N=52 | Total N=264 |
|---|---|---|---|---|---|---|
| Total AB(s) | 41 | 62 | 56 | 54 | 43 | 256 |
| Patients with AB(s) | 21 (40.4) | 29 (53.7) | 27 (50.9) | 29 (54.7) | 20 (38.5) | 126 (47.7) |
| Diarrhoea | 3 (5.8) | 2 (3.7) | 3 (5.7) | 5 (9.4) | 2 (3.8) | 15 (5.7) |
| Headache | 1 (1.9) | 4 (7.4) | 5 (9.4) | 1 (1.9) | 2 (3.8) | 13 (4.9) |
| Nausea | 4 (7.7) | 2 (3.7) | 3 (5.7) | 4 (7.5) | 0 | 13 (4.9) |
| Fatigue | 2 (3.8) | 3 (5.6) | 2 (3.8) | 2 (3.8) | 0 | 9 (3.4) |
| Mouth ulceration | 4 (7.7) | 0 | 2 (3.8) | 3 (5.7) | 0 | 9 (3.4) |
| Energy Increased | 0 | 2 (3.7) | 0 | 6 (11.3) | 0 | 8 (3.0) |
| Lethargy | 3 (5.8) | 0 | 2 (3.8) | 0 | 1 (1.9) | 6 (2.3) |
| Constipation | 1 (1.9) | 1 (1.9) | 1 (1.9) | 1 (1.9) | 1 (1.9) | 5 (1.9) |
| Dizziness | 1 (1.9) | 2 (3.7) | 1 (1.9) | 1 (1.9) | 0 | 5 (1.9) |
| Flatulence | 1 (1.9) | 2 (3.7) | 2 (3.8) | 0 | 0 | 5 (1.9) |
| Rash | 1 (1.9) | 2 (3.7) | 0 | 2 (3.8) | 0 | 5 (1.9) |

\* Preferred term is presented in this table when there were at least 5 patients under that term Figure 7: Shows that in most subjects, the increase in energy occurs while on study drug and then stops after study drug discontinuation.
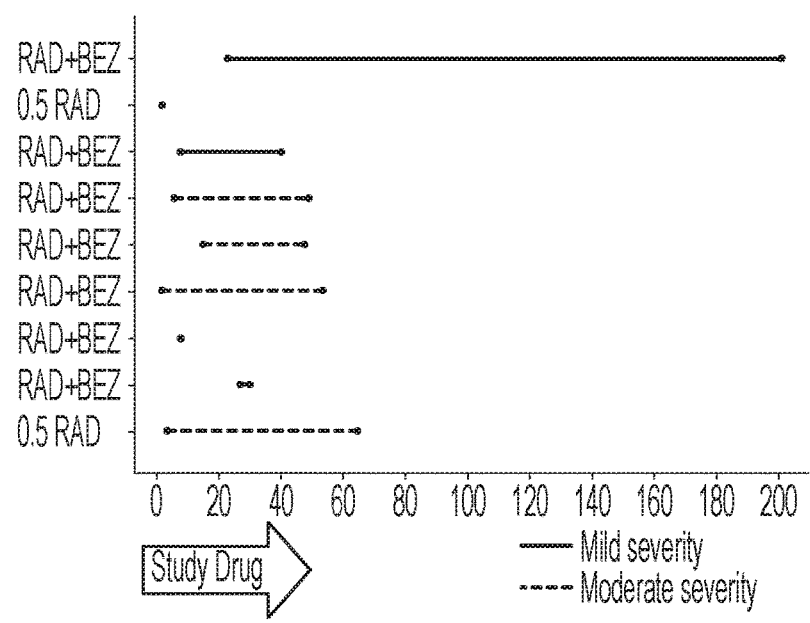

Figure 8: Subjects enrolled in CBEZ235Y2201 recorded all infections that they experienced during the study in a diary. Total infections and urinary tract infections were lowest in the RAD+BEZ combination cohort.

| Drug Cohort | RAD 0.1 mg N=57 | RAD 0.5 mg N=64 | BEZ 10 mg N=53 | RAD 0.1 mg + BEZ 10 mg N=58 | Placebo N=47 |
|---|---|---|---|---|---|
| Total Infections | 106 | 111 | 101 | 88 | 126 |
| UTIs | 7 | 9 | 2 | 0 | 8 |

Figure 9: RNAseq analysis was performed on whole blood samples obtained from elderly subjects before and after 6 weeks of placebo (9=53) or RAD001+BEZ235 (n=53) treatment. The combination of RAD001+BEZ235 led to the upregulation relative to placebo of genes that play a critical role in the innate antiviral immune response (HERC5, IFIT1, IFIT3, HERC5, RSAD2, ISG15). .
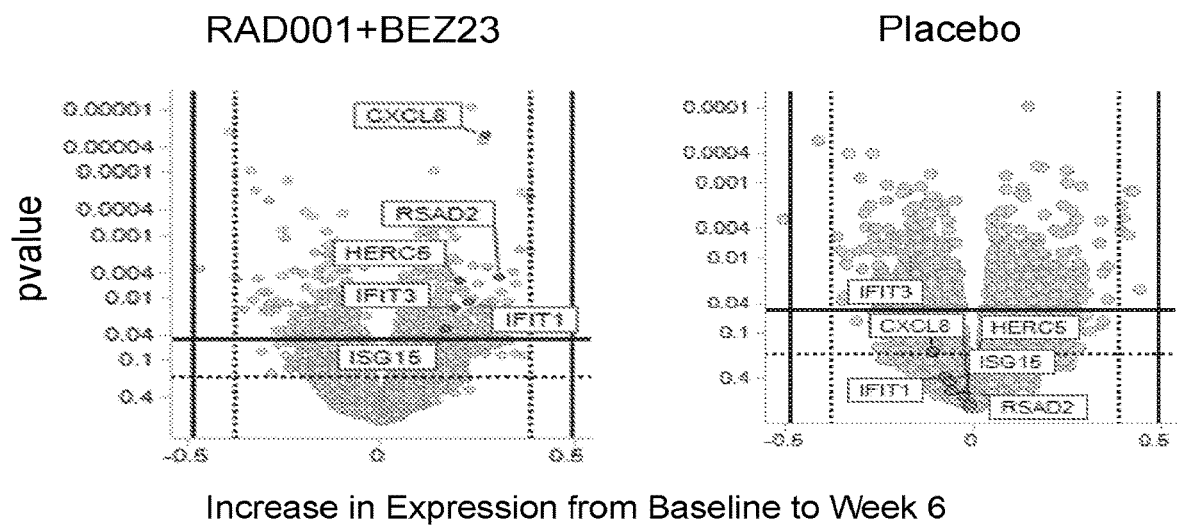

PHARMACEUTICAL COMBINATION OF EVEROLIMUS WITH DACTOLISIB

FIELD OF THE INVENTION

The present invention relates to a combination comprising (a) RAD001, or a pharmaceutically acceptable salt thereof, and (b) BEZ235, and a pharmaceutically acceptable salt thereof, for simultaneous, separate or sequential use for promotion and/or enhancement of an immune response in a subject; a pharmaceutical composition comprising such combination; a method of promoting and/or enhancing an immune response in a subject comprising administration of said combination to a subject in need thereof; use of such combination for preparation of a medicament for the promotion and/or enhancement of an immune response in a subject; and a commercial package thereto.

BACKGROUND mTOR is an evolutionarily conserved serine/threonine kinase that plays a central role in integrating environmental cues in the form of growth factors, amino acids, and energy. In the study of the immune system, mTOR is emerging as a critical regulator of immune function because of its role in sensing and integrating cues from the immune microenvironment. With the greater appreciation of cellular metabolism as an important regulator of immune cell function, mTOR is proving to be a vital link between immune function and metabolism. mTOR has the ability to direct the adaptive immune response, e.g. promoting differentiation, activation, and function in T cells, B cells, and antigen-presenting cells.

SUMMARY OF THE INVENTION

The present invention pertains to a combination comprising (a) RAD001, or a pharmaceutically acceptable salt thereof, and (b) BEZ235, or a pharmaceutically acceptable salt thereof or a pharmaceutically acceptable salt thereof, for simultaneous, separate or sequential use for the promotion and/or enhancement of an immune response in a subject.

In one aspect, the invention provides a pharmaceutical composition comprising a quantity of the COMBINATION OF THE INVENTION which is jointly therapeutically effective at promoting and/or enhancing an immune response in a subject.

In one aspect, the present invention provides a method of promoting and/or enhancing an immune response in subject comprising administering to subject in need thereof a COMBINATION OF THE INVENTION in a quantity, which is jointly therapeutically effective at promoting and/or enhancing said immune response.

In one aspect, the present invention also provides a method of treating an age related condition, comprising administering to a subject in need thereof an amount of a COMBINATION OF THE INVENTION in a quantity which is therapeutically effective to treat said age related condition.

In one aspect, the present invention provides the use of a COMBINATION OF THE INVENTION for the promotion and/or enhancement of an immune response in a subject, and for the preparation of a medicament for the promotion and/or enhancement of an immune response.

In one aspect, the present invention provides the use of a COMBINATION OF THE INVENTION for the treatment of an age related condition in a subject.

In one aspect, the present invention provides a commercial package comprising as active ingredients COMBINATION OF THE INVENTION, together with instructions for the simultaneous, separate or sequential use thereof in the promotion and/or enhancement of an immune response in a subject.

In one aspect, the present invention provides a commercial package comprising (a) RAD001, or a pharmaceutically acceptable salt thereof and instructions for the simultaneous, separate or sequential use with (b) BEZ235, or a pharmaceutically acceptable salt thereof, in the promotion and/or enhancement of an immune response in a subject.

BRIEF DESCRIPTION OF THE DRAWINGS

FIG. 1 shows the rationale for RAD+BEZ combination therapy: Synergistic inhibition of both S6K and 4EBP1.

FIG. 2 shows the synergistic inhibition of S6K is likely achieved with 0.1 mg RAD and 10 mg BEZ.

FIG. 3 shows the synergistic inhibition of 4EBP1 may be achieved with 0.1 mg RAD and 10 mg BEZ.

FIG. 4 shows a decline with age in NAD+ levels decreases sirtuin activity resulting in mitochondrial dysfunction, a decline in ATP production and subsequent aging-related organ dysfunction.

FIG. 5 shows that the RAD+BEZ increased immune response to all 3 strains of flu by over 20% (a clinically relevant increase) whereas monotherapy met this cut off for only 1 out of 3 strains.

FIG. 6 shows the increase in energy spontaneously reported by subjects predominantly in the everolimus+BEZ235 combination cohort.

FIG. 7 shows that in most subjects, the increase in energy occurs while on study drug and then stops after study drug discontinuation.

FIG. 8 shows subjects enrolled in CBEZ235Y2201 recorded all infections that they experienced during the study in a diary.

FIG. 9 shows RNAseq analysis was performed on whole blood samples obtained from elderly subjects before and after 6 weeks of placebo (9=53) or RAD001+BEZ235 (n=53) treatment.

DETAILED DESCRIPTION

The present invention pertains to a combination comprising (a) RAD001, or a pharmaceutically acceptable salt thereof, and (b) BEZ235, or a pharmaceutically acceptable salt thereof, for simultaneous, separate or sequential use for the promotion and/or enhancement of an immune response in a subject.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination" is defined herein to refer to either a fixed combination in one dosage unit form, a non-fixed combination or a kit of parts for the combined administration where RAD001, or pharmaceutically acceptable salt thereof, and BEZ235, or pharmaceutically acceptable salt thereof may be administered independently at the same time or separately within time intervals that allow that the combination partners show a cooperative, e.g., synergistic, effect.

The term "fixed combination" means that the active ingredients or therapeutic agents, e.g. RAD001 and BEZ235, are administered to a patient simultaneously in the form of a single entity or dosage form.

The term "non-fixed combination" means that the active ingredients or therapeutic agents, e.g. RAD001 and BEZ235, are both administered to a patient as separate entities or dosage forms either simultaneously, concurrently or sequentially with no specific time limits, wherein such administration provides therapeutically effective levels of the two compounds in the body of the subject, e.g., a mammal or human, in need thereof.

The term "pharmaceutical composition" is defined herein to refer to a mixture or solution containing at least one therapeutic agent to be administered to a subject, e.g., a mammal or human, in order to treat a particular disease or condition affecting the subject thereof.

The term "pharmaceutically acceptable" is defined herein to refer to those compounds, biologic agents, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The terms "combined administration" as used herein are defined to encompass the administration of the selected therapeutic agents to a single subject, e.g., a mammal or human, and are intended to include treatment regimens in which the agents are not necessarily administered by the same route of administration or at the same time.

The term "treating" or "treatment" as used herein comprises a treatment relieving, reducing or alleviating at least one symptom in a subject or affecting a delay of progression of a disease, condition and/or disorder. For example, treatment can be the diminishment of one or several symptoms of a disorder or complete eradication of a disorder. Within the meaning of the present invention, the term "treat" also denotes to arrest, delay the onset (i.e., the period prior to clinical manifestation of a disease) and/or reduce the risk of developing or worsening a disease.

The term "jointly therapeutically active" or "joint therapeutic effect" as used herein means that the therapeutic agents may be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both therapeutic agents are present in the blood of the human to be treated at least during certain time intervals.

The term "pharmaceutically effective amount" or "therapeutically effective amount" of a combination of therapeutic agents is an amount sufficient to provide an observable improvement over the baseline clinically observable signs and symptoms of the promotion and/or enhancement of the immune response.

The term "synergistic effect" as used herein refers to action of two agents such as, for example, (a) RAD001, or a pharmaceutically acceptable salt thereof, and (b) BEZ235, or a pharmaceutically acceptable salt thereof, producing an effect, for example, promoting and/or enhancing an immune response in a subject, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The term "subject" or "patient" as used herein includes animals, which are capable of promoting and/or enhancing an immune response and/or having an age related condition. Examples of subjects include mammals, e.g., humans, dogs, cows, horses, pigs, sheep, goats, cats, mice, rabbits, rats and transgenic non-human animals. In the preferred embodiment, the subject is a human, e.g., a human suffering from, at risk of suffering from, or potentially capable of suffering from an age related condition.

The term about" or "approximately" shall have the meaning of within 10%, more preferably within 5%, of a given value or range.

The term "promote" or "enhance" in the context of an immune response refers to an increase in immune response, such as an increase in the ability of immune cells to target and/or kill cancer cells, to target and/or kill pathogens and pathogen infected cells, and protective immunity following vaccination, among others. In some embodiments, protective immunity refers to the presence of sufficient immune response (such as antibody titers) to protect against subsequent infection by a pathogen expressing the same antigen or protection against a new pathogen.

The terms "immunosenescence or immunoscenescent" refer to a decrease in immune function resulting in impaired immune response, e.g., to cancer, vaccination, infectious pathogens, among others. It involves both the host's capacity to respond to infections and the development of long-term immune memory, especially by vaccination. This immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria.

Immunosenescence is a multifactorial condition leading to many pathologically significant health problems, e.g., in the aged population. Age-dependent biological changes such as a decline in function of hematopoietic stem cells, an increase in PD1+ lymphocytes, a decline in the function of phagocytes, macrophages, dendritic cells, monocytes, T cells, B cells and NK cells, and a decline in innate, cell-mediated or humoral immunity contribute to the onset of immunosenescence. In one aspect, immunosenescence can be measured in an individual by measuring telomere length in immune cells (See, e.g., U.S. Pat. No. 5,741,677). Immunosenescence can also be determined by documenting in an individual a lower than normal number of naïve CD4 and/or CD8 T cells, a decrease in early pro-B cells and pre-B cells, a decrease in T and B cell repertoire, an increase in the number of PD1-expressing T cells, e.g., a lower than normal number of PD-1 negative T cells, an increase in CD8+ CD28neg T cells, an increase in CD57+ and/or KLRG1+ CD8+ T cells, an increase in the number of LAG-3-positive T cells, a change in T cell surface glycoproteins, an increase in ICOS, CTLA-4, Tim-3 and/or LAG-3 expressing CD4 T cells, or decreased response to vaccination in a subjects they age.

The term "impaired immune response" refers to a state in which a subject does not have an appropriate immune response, e.g., to cancer, vaccination, pathogen infection, among others. In some embodiments, a subject having an impaired immune response is predicted not to get protective antibody titer levels following prophylactic vaccination, or in which a subject does not have a decrease in cell-mediated immunity or disease burden after therapeutic vaccination. A subject can also have an impaired immune response if the subject is a member of a population known to have decreased immune function or that has a history of decreased immune function such as the elderly, subjects undergoing chemotherapy treatment, asplenic subjects, immunocompromised subjects, or subjects having HIV/AIDS. Methods described herein allow for the treatment of an impaired immune response by administration of a low, immune enhancing, dose of an mTOR inhibitor, e.g., an allosteric mTOR inhibitor, such as RAD001.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number or percentage of PD-1 positive T cells and/or an increase in the number or percentage of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

a decrease in the percentage of T cells expressing the markers LAG-3, CTLA-4, ICOS or Tim-3 an increase in the expression of one or more of the following markers: $CD62L^{high}$, $CD127^{high}$, $CD27^+$, and BCL2, e.g., on memory T cells, e.g., memory T cell precursors; a decrease in the expression of KLRG1 or CD57, e.g., on naïve or memory T cells, e.g., memory T cell precursors; and an increase in the number of memory T cell precursors, e.g., cells with any one or combination of the following characteristics: increased $CD62L^{high}$, increased $CD127^{high}$, increased $CD27^+$, decreased KLRG1, and increased BCL2; wherein any of the changes described above occurs, e.g., at least transiently, e.g., as compared to a non-treated subject.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, or at least 70 but no more than 90%.

In an embodiment, a dose of an mTOR inhibitor is associated with, or provides, mTOR inhibition of at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, or at least 60 but no more than 80%.

In an embodiment, a dose of an mTOR inhibitor is associated with, or provides, mTOR inhibition of at least 5 but no more than 70%, at least 10 but no more than 70%, at least 15, but no more than 70%, at least 20 but no more than 70%, at least 30 but no more than 70%, at least 40 but no more than 70%, or at least 50 but no more than 70%.

In an embodiment, a dose of an mTOR inhibitor is associated with, or provides, mTOR inhibition of at least 5 but no more than 60%, at least 10 but no more than 60%, at least 15, but no more than 60%, at least 20 but no more than 60%, at least 30 but no more than 60%, or at least 40 but no more than 60%.

In an embodiment, a dose of an mTOR inhibitor is associated with, or provides, mTOR inhibition of at least 5 but no more than 50%, at least 10 but no more than 50%, at least 15, but no more than 50%, at least 20 but no more than 50%, at least 30 but no more than 50%, or at least 40 but no more than 50%.

In an embodiment, a dose of an mTOR inhibitor is associated with, or provides, mTOR inhibition of at least 5 but no more than 40%, at least 10 but no more than 40%, at least 15, but no more than 40%, at least 20 but no more than 40%, at least 30 but no more than 40%, or at least 35 but no more than 40%.

In an embodiment, a dose of an mTOR inhibitor is associated with, or provides, mTOR inhibition of at least 5 but no more than 30%, at least 10 but no more than 30%, at least 15, but no more than 30%, at least 20 but no more than 30%, or at least 25 but no more than 30%.

In an embodiment, a dose of an mTOR inhibitor is associated with, or provides, mTOR inhibition of at least 1, 2, 3, 4 or 5 but no more than 20%, at least 1, 2, 3, 4 or 5 but no more than 30%, at least 1, 2, 3, 4 or 5, but no more than 35, at least 1, 2, 3, 4 or 5 but no more than 40%, or at least 1, 2, 3, 4 or 5 but no more than 45%.

In an embodiment, a dose of an mTOR inhibitor is associated with, or provides, mTOR inhibition of at least 1, 2, 3, 4 or 5 but no more than 90%.

As is discussed herein, the extent of mTOR inhibition can be expressed as the extent of P70 S6K inhibition, e.g., the extent of mTOR inhibition can be determined by the level of decrease in P70 S6K activity, e.g., by the decrease in phosphorylation of a P70 S6K substrate. The level of mTOR inhibition can be evaluated by a method described herein, e.g. by the Boulay assay.

The term "promote" or "enhance" in the context of an immune response refers to an increase in immune response, such as an increase in the ability of immune cells to target and/or kill cancer cells, to target and/or kill pathogens and pathogen infected cells, and protective immunity following vaccination, among others. In some embodiments, protective immunity refers to the presence of sufficient immune response (such as antibody titers) to protect against subsequent infection by a pathogen expressing the same antigen mTOR Inhibitors As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

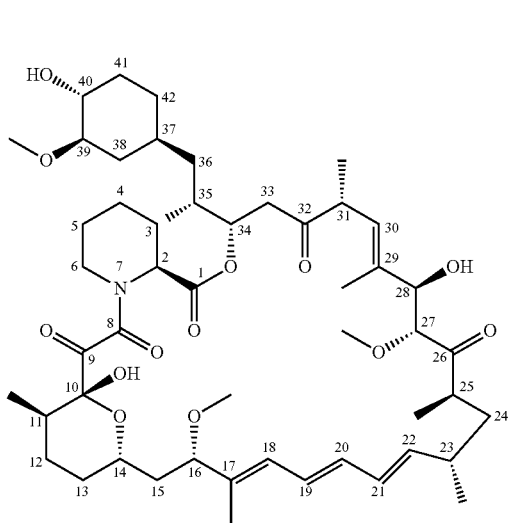

(A)

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

In mammalian cells, the target of rapamycin (mTOR) kinase exists as a multiprotein complex described as the mTORC1 complex or mTORC2 complex, which senses the availability of nutrients and energy and integrates inputs from growth factors and stress signalling. The mTORC1 complex is sensitive to allosteric mTOR inhibitors such as rapamycin, is composed of mTOR, GβL, and regulatory associated proteins of mTOR (raptor), and binds to the peptidyl-prolyl isomerase FKBP12 protein (a FK506-binding protein 1A, 12 kDa). In contrast, the mTORC2 complex is composed of mTOR, GβL, and rapamycin-insensitive companion proteins of mTOR (rictor), and does not bind to the FKBP12 protein in vitro.

The mTORC1 complex has been shown to be involved in protein translational control, operating as a growth factor and nutrient sensitive apparatus for growth and proliferation regulation. mTORC1 regulates protein translation via two key downstream substrates: P70 S6 kinase, which in turn phosphorylates ribosomal protein P70 S6, and eukaryotic translation initiation factor 4E binding protein 1 (4EBP1), which plays a key role in modulating eIF4E regulated cap-dependent translation. The mTORC1 complex regulates cell growth in response to the energy and nutrient homeostasis of the cell, and the deregulation of mTORC1 is common in a wide variety of human cancers. The function of mTORC2 involves the regulation of cell survival via phosphorylation of Akt and the modulation of actin cytoskeleton dynamics.

The mTORC1 complex is sensitive to allosteric mTOR inhibitors such as rapamycin and derivatives in large part due to rapamycin's mode of action, which involves the formation of an intracellular complex with the FKBP12 and binding to the FKBP12-rapamycin binding (FRB) domain of mTOR. This results in a conformational change in mTORC1 which is believed to alter and weaken the interaction with its scaffolding protein raptor, in turn impeding substrates such as P70 S6K1 from accessing mTOR and being phosphorylated. Rapamycin and rapalogues such as RAD001 have gained clinical relevance by inhibiting hyperactivation of mTOR associated with both benign and malignant proliferation disorders.

RAD001, otherwise known as everolimus (Afinitor®), has the chemical name (1R,9S,12S,15R,16E,18R,19R,21R, 23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29, 35-hexamethyl-11,36-dioxa-4-aza-tricyclo[30.3.1.04,9] hexatriaconta-16,24,26,28-tetraene-2,3,10,14,20-pentaone and the following chemical structure

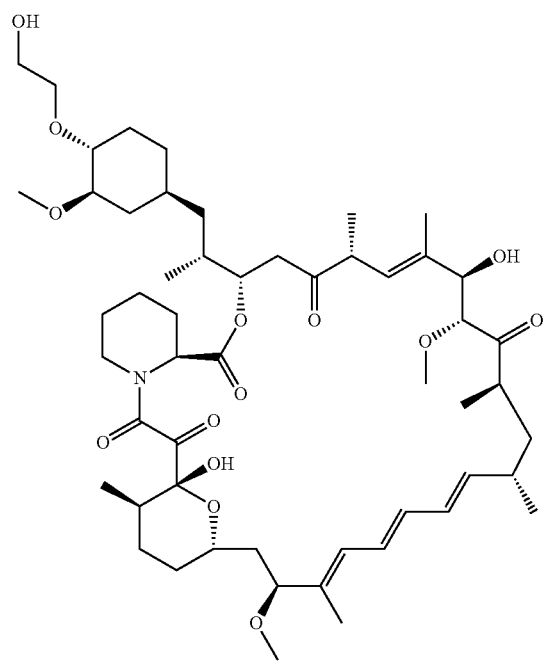 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

Everolimus is an FDA approved drug for the treatment of advanced kidney cancer and is being investigated in several other phase III clinical trials in oncology. Preclinical studies have shown that Everolimus is able to inhibit the proliferation of a wide variety of tumor cell lines both in vitro and in vivo, presumably through the suppression of rapamycin sensitive mTORC1 function. Everolimus, as a derivative of rapamycin, is an allosteric mTOR inhibitor that is highly potent at inhibiting part of the mTORC1 function, namely P70 S6 kinase (P70 S6K) and the downstream P70 S6K substrate P70 S6. Allosteric mTOR inhibitors like everolimus (and other rapamycin analogs) have little or no effect at inhibiting the mTORC2 pathway, or its resulting activation of Akt signalling. Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTOR inhibitors include zotarolimus (ABT578) and umirolimus. Alternatively or additionally, catalytic, ATP-competitive mTOR inhibitors have been found to target the mTOR kinase domain directly and target both mTORC1 and mTORC2. These are also more complete inhibitors of mTORC1 than such allosteric mTOR inhibitors as rapamycin, because they modulate rapamycin-resistant mTORC1 outputs such as 4EBP1-T37/46 phosphorylation and cap-dependent translation.

BEZ235 is a catalytic mTOR inhibitor, having the chemical name 2-methyl-2-[4-(3-methyl-2-oxo-8-quinolin-3-yl-2, 3-dihydro-imidazo[4,5-c]quinolin-1-yl)-phenyl]-propionitrile and the following chemical structure

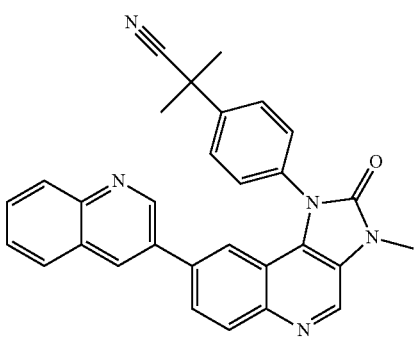

BEZ235 may also be used in its monotosylate salt form. The synthesis of BEZ235 is described in WO2006/122806.

As a catalytic mTOR inhibitor BEZ235 is capable of shutting down the complete function of mTORC1 complex, including both the rapamycin sensitive (phosphorylation of P70 S6K, and subsequently phosphorylation of P70 S6) and rapamycin insensitive (phosphorylation of 4EBP1) functions. BEZ235 has a differential effect according to the drug concentration used, whereby mTOR inhibition predominates at a low concentration (less than 100 nmol/L) but dual PI3K/mTOR inhibition at relatively higher concentrations (approximately 500 nmol/L).

The structure of the active ingredients identified by code numbers, generic or trade names may be taken from the actual edition of the standard compendium "The Merck Index" or from databases, e.g., Patents International (e.g, IMS World Publications). The corresponding content thereof is hereby incorporated by reference.

A combination comprising (a) RAD001 or a pharmaceutically acceptable salt thereof, and (b) BEZ235, or a pharmaceutically acceptable salt thereof, will be referred to hereinafter as a COMBINATION OF THE INVENTION.

In one embodiment, the invention is a combination comprising (a) RAD001 or a pharmaceutically acceptable salt thereof, and (b) BEZ235, or a pharmaceutically acceptable salt thereof, for simultaneous, separate or sequential use for the enhancement or promotion of an immune response in a subject.

In one embodiment of the COMBINATION OF THE INVENTION, RAD001 is in the neutral form. In another embodiment of the COMBINATION OF THE INVENTION, BEZ235 is the monotosylate salt. In another embodiment of the COMBINATION OF THE INVENTION, RAD001 is administered in a dosage range from 1.01-0.2 mg, e.g. 0.1 mg. In yet another embodiment of the COMBINATION OF THE INVENTION, BEZ235 is administered in a dosage range from 1-20 mg, e.g. 10 mg.

In one embodiment of the COMBINATION OF THE INVENTION, the combination is an immediate release dosage form. In another embodiment of the COMBINATION OF THE INVENTION, the combination is administered once per week. In yet another embodiment of the COMBINATION OF THE INVENTION, the combination is administered once per day.

In one embodiment of the COMBINATION OF THE INVENTION, the subject is immunocompromised. In another embodiment of the COMBINATION OF THE INVENTION, the subject is HIV+ or has AIDS. In yet another embodiment of the COMBINATION OF THE INVENTION, the subject has an infectious disease.

In one embodiment of the COMBINATION OF THE INVENTION, the subject has an impaired immune response. In another embodiment of the COMBINATION OF THE INVENTION, the subject is immunoscenescent. In yet another embodiment of the COMBINATION OF THE INVENTION, comprises treating the subject for an age related condition, e.g. immunosenescence, sarcopenia, muscle wasting, tendon stiffness, tendon injury, tendonitis, Achilles rupture, adhesive capsulitis of shoulder, plantar fasciitis, polymyalgia rheumatica, rotator cuff tear, spinal stenosis, tennis elbow, dupuytren's contractures, restless leg syndrome, osteoporosis, osteoarthritis, rheumatoid arthritis, autoimmune disease, polymyositis, gout, dementia, Huntington's disease, Alzheimer's disease, brain atrophy, aging-related mobility disability (e.g., frailty), cognitive decline, age related dementia, memory impairment, Lewy body dementia, frontotemporal dementia, Parkinson's disease, mild cognitive impairment, vascular dementia, stroke, transient ischemic attack, trigeminal neuralgia, neuropathy, sleep disorders, insomnia, atherosclerosis, arteriosclerosis, hypertension, heart dysfunction such as cardiac hypertrophy, systolic dysfunction, or diastolic dysfunction, heart failure, dilated cardiomyopathy, heart failure with preserved ejection fraction, arrhythmias, valvular heart disease, chronic obstructive pulmonary disease, chronic obstructive pulmonary disease exacerbations, pulmonary emphysema, idiopathic pulmonary fibrosis, pulmonary hypertension, pulmonary embolism, dyspnea, liver disease including NASH and cirrhosis, gallstones, kidney stones, Barrett's esophagus, hemorrhoids, decubitus ulcers, diverticulitis, constipation, colonic polyps, hemorrhoids, fecal incontinence, cachexia, malabsorption, erectile dysfunction, loss of libido, cataracts, age-related macular degeneration, glaucoma, retinal degeneration, retinal detachment, dry eye, presbyopia, falls, vertigo, benign prostatic hypertrophy, prostate cancer, diminished life expectancy, impaired kidney function, chronic renal failure, acute renal failure, glomerulosclerosis, glomerulosclerosis, nephrosclerosis, dehydration, neurogenic bladder, urinary tract infections, cystitis, urinary incontinence, cancer, obesity, metabolic syndrome, prediabetes, diabetes skin atrophy, skin aging, wrinkles, seborrheic keratosis, actinic keratosis, skin cancer, sun-damaged skin, rosacea, onychomycosis, greying of hair, baldness, age-related hearing loss, tinnitus, loss of smell, periodontal disease, tooth decay, dry mouth, thyroid disease, diseases associated with mitochondrial dysfunction, premature aging syndromes and progerias including Werner's syndrome and Hutchinson Guilford Progeria Syndrome, anemia, folic acid-deficiency anemia, coagulopathy, deep venous thrombosis, cachexia, depression and diminished life expectancy.

In one embodiment of the invention, the invention is a pharmaceutical composition comprising a COMBINATION OF THE INVENTION and at least one pharmaceutically acceptable carrier.

In another embodiment of the invention, the invention is a method of promoting or enhancing an immune response in a subject which comprises administering to said subject a COMBINATION OF THE INVENTION in a quantity which is jointly therapeutically effective at promoting or enhancing an immune response.

In yet another embodiment of the invention, the invention is a method of treating a subject having an age related condition which comprises administering to said subject a COMBINATION OF THE INVENTION in a quantity which is jointly therapeutically effective against said age related condition, e.g. sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age related dementia, memory impairment, tendon stiffness, heart dysfunction such as cardiac hypertrophy and systolic and diastolic dysfunction, immunosenescence, cancer, obesity, and diabetes.

In one embodiment of the invention, the invention is the use of the COMBINATION OF THE INVENTION for the preparation of a medicament for the promotion or enhancement of an immune response.

In another embodiment, the invention is the use of the COMBINATION OF THE INVENTION for the preparation of a medicament for the treatment of an age related condition, e.g. sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age related dementia, memory impairment, tendon stiffness, heart dysfunction such as cardiac hypertrophy and systolic and diastolic dysfunction, immunosenescence, cancer, obesity, and diabetes.

In one embodiment, the invention is a commercial package comprising RAD001, or a pharmaceutically acceptable salt thereof and instructions for the simultaneous, separate or sequential use with BEZ235, or a pharmaceutically acceptable salt thereof, in the promotion or enhancement of an immune response.

In another embodiment, the invention is a commercial package comprising RAD001, or a pharmaceutically acceptable salt thereof and instructions for the simultaneous, separate or sequential use with BEZ235, or a pharmaceutically acceptable salt thereof, in the treatment of an age related condition.

A further benefit is that lower doses of the active ingredients of the COMBINATION OF THE INVENTION can be used, for example, that the dosages need not only often be smaller, but are also applied less frequently, or can be used in order to diminish the incidence of side-effects observed with one of the combination partners alone. This is in accordance with the desires and requirements of the patients to be treated.

It can be shown by established test models that a COMBINATION OF THE INVENTION results in the beneficial effects described herein before. The person skilled in the art is fully enabled to select a relevant test model to prove such beneficial effects. The pharmacological activity of a COMBINATION OF THE INVENTION may, for example, be demonstrated in a clinical study or in an in vivo or in vitro test procedure as essentially described hereinafter.

In one aspect, the invention provides a pharmaceutical composition comprising a quantity, which is jointly therapeutically effective at promoting and/or enhancing an immune response in a subject, of the COMBINATION OF THE INVENTION. In this composition, the combination partners (a) and (b) are administered in a single formulation or unit dosage form by any suitable route. The unit dosage form may also be a fixed combination.

In a further aspect, the invention provides pharmaceutical compositions separately comprising a quantity, which is jointly therapeutically effective at promoting and/or enhancing an immune response in a subject, of combination partner (a) and combination partner (b) which are administered concurrently but separately, or administered sequentially.

The pharmaceutical compositions for separate administration of the combination partners, or for the administration in a fixed combination, i.e. a single galenical composition comprising the COMBINATION OF THE INVENTION, may be prepared in a manner known per se and are those suitable for enteral (such as oral or rectal) and parenteral administration to subjects and comprising a therapeutically effective amount of at least one combination partner alone, e.g. as indicated above, or in combination with one or more pharmaceutically acceptable carriers.

The novel pharmaceutical composition contains may contain, from about 0.1% to about 99.9%, preferably from about 1% to about 60%, of the active ingredient(s).

In yet another embodiment, the invention is the COMBINATION OF THE INVENTION, according to any of the preceding embodiments, wherein the subject is greater than 65 years of age.

In another embodiment, the invention is the COMBINATION OF THE INVENTION, according to any of the preceding embodiments, wherein the subject has COPD.

Chronic obstructive pulmonary disease (COPD) is a lung disease characterized by chronic obstruction of lung airflow that interferes with normal breathing and is not fully reversible. The more familiar terms 'chronic bronchitis' and 'emphysema' are no longer used, but are now included within the COPD diagnosis. COPD is not simply a "smoker's cough" but an under-diagnosed, life-threatening lung disease. A COPD diagnosis is confirmed by a simple test called spirometry, which measures how deeply a person can breathe and how fast air can move into and out of the lungs. Such a diagnosis should be considered in any patient who has symptoms of cough, sputum production, or dyspnea (difficult or labored breathing), and/or a history of exposure to risk factors for the disease. Where spirometry is unavailable, the diagnosis of COPD should be made using all available tools. Clinical symptoms and signs, such as abnormal shortness of breath and increased forced expiratory time, can be used to help with the diagnosis. A low peak flow is consistent with COPD, but may not be specific to COPD because it can be caused by other lung diseases and by poor performance during testing. Chronic cough and sputum production often precede the development of airflow limitation by many years, although not all individuals with cough and sputum production go on to develop COPD.

In another embodiment, the invention is the COMBINATION OF THE INVENTION, according to any of the preceding embodiments, wherein the subject resides in a nursing home facility.

In yet another embodiment, the invention is the COMBINATION OF THE INVENTION, according to any of the preceding embodiments, wherein the subject is residing in an assisted living facility.

In yet another embodiment, the invention is the COMBINATION OF THE INVENTION, according to any of the preceding embodiments, wherein the subject resides in a skilled nursing facility.

In yet another embodiment, the invention is the COMBINATION OF THE INVENTION, according to any of the preceding embodiments, wherein the subject resides in a rehabilitation facility.

In yet another embodiment, the invention is the COMBINATION OF THE INVENTION, according to any of the preceding embodiments, wherein the subject requires assistance with one or more activity of daily living.

Activities of daily living (ADL) are routine activities that people tend do every day without needing assistance. There are six basic ADLs: eating, bathing, dressing, toileting, transferring (walking) and continence. An individual's ability to perform ADLs is important for determining what type of long-term care (e.g. nursing-home care or home care) and coverage the individual needs (i.e. Medicare, Medicaid or long-term care insurance).

ADLs (activities of daily living): The things we normally do in daily living including any daily activity we perform for self-care such as feeding ourselves, bathing, dressing, grooming, work, homemaking, and leisure. The ability or inability to perform ADLs can be used as a very practical measure of ability/disability in many disorders.

In yet another embodiment, the invention is the COMBINATION OF THE INVENTION, according to any of the preceding embodiments, wherein the subject When the subject has mobility disability.

Mobility disability or mobility impairment refers to the inability of a person to use one or more of his/her extremities, or a lack of strength to walk, grasp, or lift objects. The use of a wheelchair, crutches, or a walker may be utilized to aid in mobility. Mobility impairment may be caused by a number of factors, such as disease, an accident, or a congenital disorder and may be the result from neuro-muscular and orthopaedic impairments.

Pharmaceutical compositions for the combination therapy, including fixed combinations or non-fixed combinations, for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, granulating, sugar-coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units. It will be further appreciated that the unit content of a combination partner for parenteral administration may contain a higher dosage amount of the combination partner which is diluted to the effective dosage amount before administration.

A unit dosage form containing the combination of agents or individual agents of the combination of agents may be in the form of micro-tablets enclosed inside a capsule, e.g. a gelatin capsule. For this, a gelatin capsule as is employed in pharmaceutical formulations can be used, such as the hard gelatin capsule known as CAPSUGEL™, available from Pfizer.

The unit dosage forms of the present invention may optionally further comprise additional conventional carriers or excipients used for pharmaceuticals. Examples of such carriers include, but are not limited to, disintegrants, binders, lubricants, glidants, stabilizers, and fillers, diluents, colorants, flavours and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See *The Handbook of Pharmaceutical Excipients*, 4*th* edition, Rowe et al., Eds., American Pharmaceuticals Association (2003); and *Remington: the Science and Practice of Pharmacy*, 20*th* edition, Gennaro, Ed., Lippincott Williams & Wilkins (2003).

These optional additional conventional carriers may be incorporated into the oral dosage form either by incorporating the one or more conventional carriers into the initial mixture before or during melt granulation or by combining the one or more conventional carriers with the granules in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL™ from International Specialty Products (Wayne, N.J.); cross-linked sodium carboxymethylcellulose or croscarmellose sodium, e.g., AC-DI-SOL™ from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH™ from FMC (Philadelphia, Pa.), hydroxypropyl cellulose hydroxylethyl cellulose and hydroxylpropylmethyl cellulose METHOCEL™ from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

The optimum ratios, individual and combined dosages, and concentrations of the therapeutic agents of the COMBINATION OF THE INVENTION that yield efficacy without toxicity are based on the kinetics of the therapeutic agent's availability to target sites, and are determined using methods known to those of skill in the art.

In accordance with the present invention, a therapeutically effective amount of each of the therapeutic agents of the COMBINATION OF THE INVENTION may be administered simultaneously or sequentially and in any order, and the components may be administered separately or as a fixed combination. For example, the method of treating an infection or aging-related disease according to the invention may comprise (i) administration of the first agent (a) in free or pharmaceutically acceptable salt form, and (ii) administration of an agent (b) in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual therapeutic agents of the COMBINATION OF THE INVENTION may be administered separately at different times during the course of therapy or concurrently in divided or single combination forms. Furthermore, the term "administering" also encompasses the use of a pro-drug of a therapeutic agent that convert in vivo to the therapeutic agent as such. The instant invention is therefore to be understood as embracing all such regimens of simultaneous or alternating treatment and the term "administering" is to be interpreted accordingly.

The effective dosage of each of the therapeutic agents employed in the COMBINATION OF THE INVENTION may vary depending on the particular therapeutic agent or pharmaceutical composition employed the mode of administration, the condition being treated, and the severity of the condition being treated. Thus, the dosage regimen of the COMBINATION OF THE INVENTION is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition.

The effective dosage of each of the therapeutic agents of the COMBINATION OF THE INVENTION may require more frequent administration of one of the therapeutic agent(s) as compared to the other therapeutic agent(s) in the combination. Therefore, to permit appropriate dosing, packaged pharmaceutical products may contain one or more dosage forms that contain the combination of compounds, and one or more dosage forms that contain one of the combination of therapeutic agent(s), but not the other therapeutic agent(s) of the combination.

When the combination partners, which are employed in the COMBINATION OF THE INVENTION, are applied in the form as marketed as single drugs, their dosage and mode of administration can be in accordance with the information provided on the package insert of the respective marketed drug, if not mentioned herein otherwise.

RAD001, particularly its free form, is preferably administered orally at a dose in the range from about 0.01 mg to about 1 mg daily and/or weekly. In a preferred embodiment, the dosage of RAD001, particularly its free form, is administered orally at a dosage of 0.1 mg/daily to an adult person.

BEZ235, particularly its P-Toluenesulfonate salt, is preferably administered orally at a dose in the range from about 1 mg/to about 20 mg daily and/or weekly. In a preferred embodiment, the dosage of BEZ235, particularly its P-Toluenesulfonate salt, is administered orally at a dosage of 10 mg daily to an adult person.

The optimal dosage of each therapeutic agent for promotion and/or enhancement of an immune response in a subject and/or treating an age related condition is a subject can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each therapeutic agent that may be combined with the carrier materials to produce a single dosage form will vary depending upon the individual treated and the particular mode of administration. In some embodiments the unit dosage forms containing the combination of therapeutic agents as described herein will contain the amounts of each agent of the combination that are typically administered when the therapeutic agents are administered alone.

Frequency of dosage may vary depending on the therapeutic agent used and the particular condition to be treated. In general, the use of the minimum dosage that is sufficient to provide effective therapy is preferred. Patients may generally be monitored for therapeutic effectiveness using assays suitable for the condition being treated, which will be familiar to those of ordinary skill in the art.

In one aspect, the present invention provides a method of promoting and/or enhancing and immune response in a subject comprising administering to subject in need thereof a COMBINATION OF THE INVENTION in a quantity, which is jointly therapeutically effective at promoting and/or enhancing an immune response in a subject.

Moreover, the present invention also provides a method of treatment of an age related condition in a subject, comprising administering to a subject in need thereof an amount of a COMBINATION OF THE INVENTION in a quantity which is therapeutically effective to treat an age related condition In one aspect, the present invention provides the use of a COMBINATION OF THE INVENTION for the enhancement and/or promotion of an immune response and/or for the preparation of a medicament for the enhancement and/or promotion of an immune response.

In one aspect, the present invention provides the use of a COMBINATION OF THE INVENTION for the treatment of an age related condition and/or for the preparation of a medicament for the treatment of an age related condition.

In one aspect, the present invention provides a commercial package comprising as active ingredients COMBINATION OF THE INVENTION, together with instructions for the simultaneous, separate or sequential use thereof in the enhancement and/or treatment of an immune response.

In another aspect, the present invention provides a commercial package comprising as active ingredients COMBINATION OF THE INVENTION, together with instructions for the simultaneous, separate or sequential use thereof in the treatment of an age related condition.

In one aspect, the present invention provides a commercial package comprising RAD001, or a pharmaceutically acceptable salt thereof, and instructions for the simultaneous, separate or sequential use with BEZ235 or a pharmaceutically acceptable salt thereof, in the enhancement and/or promotion of an immune response.

In another aspect, the present invention provides a commercial package comprising RAD001, or a pharmaceutically acceptable salt thereof, and instructions for the simultaneous, separate or sequential use with BEZ235 or a pharmaceutically acceptable salt thereof, in the treatment of an age related condition.

Pathogenic Infections

In another aspect, the methods provided herein can be used to treat infection by a pathogen in a subject. In some embodiments, the pathogen is a viral pathogen, e.g., a viral pathogen e.g. HIV, meningitis causing viruses, encephalitis causing viruses, Hepatitis A, Hepatitis B, Hepatitis C, rabies virus, polio virus, influenza virus, parainfluenza virus, adenovirus, rhinovirus, measles virus, mumps virus, rubella, pertussis, papilloma virus, yellow fever virus, respiratory syncytial virus, parvovirus, Norwalk virus, chikungunya virus, hemorrhagic fever viruses including Ebola virus, dengue virus, Zika virus, and Herpes viruses, e.g., varicella, cytomegalovirus and Epstein-Barr virus. In some embodiments, the infection is a viral infection, such as a chronic viral infection. In some embodiments, a chronic viral infection is selected from Hepatitis A, Hepatitis B, Hepatitis C, Epstein Barr Virus, HIV, Cytomegalovirus, Herpes Simplex Virus 1, Herpes Simplex Virus 2, Human Papillomavirus, Adenovirus, and Kaposi's Sarcoma-Associated Herpesvirus. In some embodiments, a chronic viral infection comprises HIV.

For example, Lichterfeld and colleagues observed that HIV-specific CD8+ T-cells showed reduced telomere length and an increase in telomere length and telomerase activity upon inhibition of PD-1 (see e.g., Lichterfeld, M et al. (2008) Blood 112(9):3679-3687). In another example, PD-1 was significantly upregulated in hepatitis C (HVC)-specific CD8+ cytotoxic T lymphocytes (see e.g., Golden-Mason, L (2007) J. Virol. 81(17): 9249-9258). In some embodiments, a viral infection comprises a viral respiratory tract infection. In some embodiments viral respiratory tract infection is caused by a rhinovirus, coronavirus, influenza virus, respiratory syncytial virus (RSV), adenovirus, and/or parainfluenza. In some embodiments, a viral respiratory tract infection is pneumonia. In some embodiments, a viral respiratory tract infection includes a lung abscess. In some embodiments, a viral respiratory tract infection includes bronchitis. In some embodiments, the pathogen is a bacterial pathogen, e.g., a bacterial pathogen selected from *Meningococcus, Haemophilus, Pneumococcus, Staphylococcus, Streptococcus, Neisseria, Moraxella, Escherichia coli, Klebsiella, Pseudomonas, Enterobacter, Proteus, Serratia, Legionella, Salmonella, Shigella, Acinetobacer, Listeria, Chlamydia,* and *Mycobacterium* among others.

In some embodiments, the pathogen is a parasitic pathogen, e.g., *Toxoplasma, Leishmania* and malaria, *T. cruzii,* Helminth, e.g., *Schistosoma.*

In some embodiments, the pathogen is a yeast or fungal pathogen, e.g., *Candida, Cryptococcus oCoccidioides, Blastomyces, aspergillus,* or *mucormycetes.*

Senescence and Other Disorders

In another aspect, the methods provided herein can be used to treat senescence in a subject. As used herein, the term "senescence" is meant to include all types of aging. In some embodiments, senescence comprises immunosenescence. Immunosenescence includes reduced immune response to infection with age and results from thymic involution in T-cell lineages, resulting in decreased T cell production and export (see e.g., Shimatani, K et al. (2009) PNAS 106 (37):15807-15812). In some embodiments, there is an increase in population of a bona fide age-dependent CD4+ or CD8+ T cell population defined by a persistent expression of PD-1, which inhibits T cell responses to antigens (see e.g., Shimatani, K et al. (2009) PNAS 106 (37):15807-15812; Nunes, C et al. (2012) Clinical Cancer Research 18(3):678-687). In some embodiments, senescence comprises cellular senescence, in which a cell no longer divides. In some embodiments, age-related immunosenescence comprises decreased production of naive lymphocytes by hematopoietic stem cells (Chen, Science Signalling, ra75, 2009). Cellular senescence is correlated with the progressive shortening of telomeres that occurs with each cell division or the intracellular expression of p16. In some embodiments senescence comprises an age-related decrease in the function of neutrophils, lymphocytes, NK cells, macrophages and/or dendritic cells (see e.g. Boraschi D et al. (2013) Sci Transl Med 5(185):ps8; Kumar R and Burns EA. (2008) Expert Rev. Vaccines 7(4): 467-479).

The term "age-related condition" refers to any disease, disorder, or pathology whose incidence in a population or severity in an individual correlates with the progression of age. More specifically, an age-related condition is a disease, disorder, or pathology whose incidence is at least 1.5 fold higher among human individuals greater than 60 years of age relative to human individuals between the ages of 20-30 and in a selected population of greater than 100,000 individuals. In one aspect, the invention relates to the treatment of conditions including, but not limited to immunosenescence, sarcopenia, muscle wasting, tendon stiffness, tendon injury, tendonitis, Achilles rupture, adhesive capsulitis of shoulder, plantar fasciitis, polymyalgia rheumatica, rotator cuff tear, spinal stenosis, tennis elbow, dupuytren's contractures, restless leg syndrome, osteoporosis, osteoarthritis, rheumatoid arthritis, autoimmune disease, polymyositis, gout, dementia, Huntington's disease, Alzheimer's disease, brain atrophy, aging-related mobility disability (e.g., frailty), cognitive decline, age related dementia, memory impairment, Lewy body dementia, frontotemporal dementia, Parkinson's disease, mild cognitive impairment, vascular dementia, stroke, transient ischemic attack, trigeminal neuralgia, neuropathy, sleep disorders, insomnia, atherosclerosis, arteriosclerosis, hypertension, heart dysfunction such as cardiac hypertrophy, systolic dysfunction, or diastolic dysfunction, heart failure, dilated cardiomyopathy, heart failure with preserved ejection fraction, arrhythmias, valvular heart disease, chronic obstructive pulmonary disease, chronic obstructive pulmonary disease exacerbations, pulmonary emphysema, idiopathic pulmonary fibrosis, pulmonary hypertension, pulmonary embolism, dyspnea, liver disease including NASH and cirrhosis, gallstones, kidney stones, Barrett's esophagus, hemorrhoids, decubitus ulcers, diverticulitis, constipation, colonic polyps, hemorrhoids, fecal incontinence, cachexia, malabsorption, erectile dysfunction, loss of libido, cataracts, age-related macular degeneration, glaucoma, retinal degeneration, retinal detachment, dry eye, presbyopia, falls, vertigo, benign prostatic hypertrophy, prostate cancer, diminished life expectancy, impaired kidney function, chronic renal failure, acute renal failure, glomerulosclerosis, glomerulosclerosis, nephrosclerosis, dehydration, neurogenic bladder, urinary tract infections, cystitis, urinary incontinence, cancer, obesity, metabolic syndrome, prediabetes, diabetes skin atrophy, skin aging, wrinkles, seborrheic keratosis, actinic keratosis, skin cancer, sun-damaged skin, rosacea, onychomycosis, greying of hair, baldness, age-related hearing loss, tinnitus, loss of smell, periodontal disease, tooth decay, dry mouth, thyroid disease, diseases associated with mitochondrial dysfunction, premature aging syndromes and progerias including Werner's syndrome and Hutchinson Guilford Progeria Syndrome, anemia, folic acid-deficiency anemia, coagulopathy, deep venous thrombosis, cachexia, depression, and diminished life expectancy.

EXAMPLES

The following Examples illustrate the invention described above; they are not, however, intended to limit the scope of the invention in any way. The beneficial effects of the pharmaceutical combination of the present invention can also be determined by other test models known as such to the person skilled in the pertinent art.

Utility of the COMBINATION OF THE PRESENT INVENTION, as described herein, may be demonstrated in vitro, in animal test methods as well as in clinical studies. For example in the utility of the compounds of formula (I) in accordance with the present invention may be demonstrated in accordance with the methods hereinafter described:

Example 1: Synergistic Effect OF RAD001 and BEZ235 Combination

In a clinical study elderly volunteers were treated for 6 weeks daily with one of four mTOR inhibitor dosing regimens: 0.5 mg/day RAD001, 0.1 mg/day RAD001, 10 mg/day BEZ235 or 0.1 mg/day RAD001+10 mg/day BEZ235. The combination treatment arm was included because RAD001 and BEZ235 have been shown to synergistically inhibit S6K and 4EBP1 pathways downstream of mTOR in vitro, see FIGS. 1, 2 and 3.

After being dosed for 6 weeks, the elderly volunteers were given a 2 week drug-free break and then received influenza vaccination. Results of the study indicate that mTOR inhibitor therapy enhanced the response to influenza vaccination with the greatest efficacy seen in the 0.1 mg RAD001+10 mg BEZ235 combination arm. The GMT ratio as compared to placebo 4 weeks after vaccination was >1.2 for 3/3 vaccine strains in the RAD001+BEZ235 combination arm, for ⅓ strains in the RAD001 0.1 and 0.5 mg monotherapy arms, and for 0/3 strains in the BEZ235 monotherapy arms, see FIG. 4 which shows that RAD+BEZ increased immune response to all 3 strains of flu by over 20% (a clinically relevant increase) whereas monotherapy met this cut off for only 1 out of 3 strains. All dosing regimens were relatively well tolerated. Higher rates of mouth ulcers, nausea, diarrhoea and rash were seen in the mTOR inhibitor cohorts as compared to the placebo cohort. However the majority of these adverse events were of mild severity, transient and resolved despite continued dosing of mTOR inhibitors.

As part of the study, subjects were asked to record all infections in diaries. The total number of infections as well as the number of urinary tract infections was lowest in the 0.1 mg RAD001 and 10 mg BEZ235 combination arm. In a post-hoc analysis, the incidence and severity of respiratory tract infections were reduced in all mTOR inhibitor treatment arms as compared to placebo. The decrease was greatest during the 6 weeks subjects were on study drug.

In the trial, a subset of subjects spontaneously reported an increase in energy/exercise ability while on study drug. The majority of subjects spontaneously reporting an increase in energy were in the cohort treated with a combination of RAD001+BEZ235. No subjects treated with placebo spontaneously reported an increase in energy, see FIGS. 5 and 6 which show that most of the subjects who spontaneously reported an increase in energy were in the RAD+BEZ cohort.

Enumerated Embodiments

In a first embodiment, the invention is a combination comprising (a) RAD001 or a pharmaceutically acceptable salt thereof, and (b) BEZ235, or a pharmaceutically acceptable salt thereof, for simultaneous, separate or sequential use for the enhancement or promotion of an immune response in a subject.

In a second embodiment, the invention is the combination according to the first embodiment, wherein RAD001 is in the neutral form.

In a third embodiment, the invention is the combination of either the first or second embodiments, wherein BEZ235 is the monotosylate salt.

In a fourth embodiment, the invention is the combination according to any one of the first through third embodiments, comprising the administration of 0.01-0.2 mg of RAD001.

In a fifth embodiment, the invention is the combination according to any one of the first through fourth embodiments, comprising the administration of 0.1 mg of RAD001.

In a sixth embodiment, the invention is the combination according to any one of the first through fifth embodiments, comprising the administration of 1-20 mg of BEZ235.

In a seventh embodiment, the invention is the combination according to any one of the first through sixth embodiments, comprising the administration of 10 mg of BEZ235.

In an eighth embodiment, the invention is the combination according to any one of the first through seventh embodiments, wherein said combination is an immediate release dosage form.

In a ninth embodiment, the invention is the combination according to any one of the first through seventh embodiments, wherein said combination is a sustained release dosage form.

In a tenth embodiment, the invention is the combination according to any one of the first through ninth embodiments, wherein said combination is administered once per week.

In an eleventh embodiment, the invention is the combination according to any one of the first through ninth embodiments, wherein said combination is administered once per day.

In a twelfth embodiment, the invention is the combination according to any one of the first through eleventh embodiments, wherein the subject is immunocompromised.

In a thirteenth embodiment, the invention is the combination according to any one of the first through eleventh embodiments, wherein the subject is HIV+ or has AIDs.

In a fourteenth embodiment, the invention is the combination according to any one of the first through eleventh embodiments, wherein the subject has an infectious disease.

In a fifteenth embodiment, the invention is the combination according to any one of the first through eleventh embodiments, wherein the subject has an impaired immune response.

In a sixteenth embodiment, the invention is the combination according to any one of the first through eleventh embodiments, wherein the subject is immunoscenescent.

In a seventeenth embodiment, the invention is the combination according to any one of the first through eleventh embodiments, comprising treating the subject for an age related condition.

In an eighteenth embodiment, the invention is the combination of the seventeenth embodiment, wherein the age related condition is selected from the group consisting of immunosenescence, sarcopenia, muscle wasting, tendon stiffness, tendon injury, tendonitis, Achilles rupture, adhesive capsulitis of shoulder, plantar fasciitis, polymyalgia rheumatica, rotator cuff tear, spinal stenosis, tennis elbow, dupuytren's contractures, restless leg syndrome, osteoporosis, osteoarthritis, rheumatoid arthritis, autoimmune disease, polymyositis, gout, dementia, Huntington's disease, Alzheimer's disease, brain atrophy, aging-related mobility disability (e.g., frailty), cognitive decline, age related dementia, memory impairment, Lewy body dementia, frontotemporal dementia, Parkinson's disease, mild cognitive impairment, vascular dementia, stroke, transient ischemic attack, trigeminal neuralgia, neuropathy, sleep disorders, insomnia, atherosclerosis, arteriosclerosis, hypertension, heart dysfunction such as cardiac hypertrophy, systolic dysfunction, or diastolic dysfunction, heart failure, dilated cardiomyopathy, heart failure with preserved ejection fraction, arrhythmias, valvular heart disease, chronic obstructive pulmonary disease, chronic obstructive pulmonary disease exacerbations, pulmonary emphysema, idiopathic pulmonary fibrosis, pulmonary hypertension, pulmonary embolism, dyspnea, liver disease including NASH and cirrhosis, gallstones, kidney stones, Barrett's esophagus, hemorrhoids, decubitus ulcers, diverticulitis, constipation, colonic polyps, hemorrhoids, fecal incontinence, cachexia, malabsorption, erectile dysfunction, loss of libido, cataracts, age-related macular degeneration, glaucoma, retinal degeneration, retinal detachment, dry eye, presbyopia, falls, vertigo, benign prostatic hypertrophy, prostate cancer, diminished life expectancy, impaired kidney function, chronic renal failure, acute renal failure, glomerulosclerosis, glomerulosclerosis, nephrosclerosis, dehydration, neurogenic bladder, urinary tract infections, cystitis, urinary incontinence, cancer, obesity, metabolic syndrome, prediabetes, diabetes skin atrophy, skin aging, wrinkles, seborrheic keratosis, actinic keratosis, skin cancer, sun-damaged skin, rosacea, onychomycosis, greying of hair, baldness, age-related hearing loss, tinnitus, loss of smell, periodontal disease, tooth decay, dry mouth, thyroid disease, diseases associated with mitochondrial dysfunction, premature aging syndromes and progerias including Werner's syndrome and Hutchinson Guilford Progeria Syndrome, anemia, folic acid-deficiency anemia, coagulopathy, deep venous thrombosis, cachexia, depression, and diminished life expectancy.

In a nineteenth embodiment, the invention is a pharmaceutical composition comprising a combination according to any one of the first through eleventh embodiments, and at least one pharmaceutically acceptable carrier.

In a twentieth embodiment, the invention is a method of promoting or enhancing an immune response in a subject which comprises administering to said subject a combination according to any one of the first through eleventh embodiments in a quantity which is jointly therapeutically effective at promoting or enhancing an immune response.

In a twenty-first embodiment, the invention is a method of treating a subject having an age related condition which comprises administering to said subject a combination according to any one of the first through eleventh embodiments in a quantity which is jointly therapeutically effective against said age related condition.

In a twenty-second embodiment, the invention is a method according to the twenty-first embodiment, wherein the age related condition is selected from the group consisting of immunosenescence, sarcopenia, muscle wasting, tendon stiffness, tendon injury, tendonitis, Achilles rupture, adhesive capsulitis of shoulder, plantar fasciitis, polymyalgia rheumatica, rotator cuff tear, spinal stenosis, tennis elbow, dupuytren's contractures, restless leg syndrome, osteoporosis, osteoarthritis, rheumatoid arthritis, autoimmune disease, polymyositis, gout, dementia, Huntington's disease, Alzheimer's disease, brain atrophy, aging-related mobility disability (e.g., frailty), cognitive decline, age related dementia, memory impairment, Lewy body dementia, frontotemporal dementia, Parkinson's disease, mild cognitive impairment, vascular dementia, stroke, transient ischemic attack, trigeminal neuralgia, neuropathy, sleep disorders, insomnia, atherosclerosis, arteriosclerosis, hypertension, heart dysfunction such as cardiac hypertrophy, systolic dysfunction, or diastolic dysfunction, heart failure, dilated cardiomyopathy, heart failure with preserved ejection fraction, arrhythmias, valvular heart disease, chronic obstructive pulmonary disease, chronic obstructive pulmonary disease exacerbations, pulmonary emphysema, idiopathic pulmonary fibrosis, pulmonary hypertension, pulmonary embolism, dyspnea, liver disease including NASH and cirrhosis, gallstones, kidney stones, Barrett's esophagus, hemorrhoids, decubitus ulcers, diverticulitis, constipation, colonic polyps, hemorrhoids, fecal incontinence, cachexia, malabsorption, erectile dysfunction, loss of libido, cataracts, age-related macular degeneration, glaucoma, retinal degeneration, retinal detachment, dry eye, presbyopia, falls, vertigo, benign prostatic hypertrophy, prostate cancer, diminished life expectancy, impaired kidney function, chronic renal failure, acute renal failure, glomerulosclerosis, glomerulosclerosis, nephrosclerosis, dehydration, neurogenic bladder, urinary tract infections, cystitis, urinary incontinence, cancer, obesity, metabolic syndrome, prediabetes, diabetes skin atrophy, skin aging, wrinkles, seborrheic keratosis, actinic keratosis, skin cancer, sun-damaged skin, rosacea, onychomycosis, greying of hair, baldness, age-related hearing loss, tinnitus, loss of smell, periodontal disease, tooth decay, dry mouth, thyroid disease, diseases associated with mitochondrial dysfunction, premature aging syndromes and progerias including Werner's syndrome and Hutchinson Guilford Progeria Syndrome, anemia, folic acid-deficiency anemia, coagulopathy, deep venous thrombosis, cachexia, depression, and diminished life expectancy.

In a twenty-third embodiment, the invention is the use of the combination according to any one of the first through eleventh embodiments for the preparation of a medicament for the promotion or enhancement of an immune response.

In a twenty-fourth embodiment, the invention is the use of the combination according to any one of the first through eleventh embodiments for the preparation of a medicament for the treatment of an age related condition.

In a twenty-fifth embodiment, the invention is the use of the combination according to the twenty-fourth embodiment wherein the age related condition is selected from the group consisting of immunosenescence, sarcopenia, muscle wasting, tendon stiffness, tendon injury, tendonitis, Achilles rupture, adhesive capsulitis of shoulder, plantar fasciitis, polymyalgia rheumatica, rotator cuff tear, spinal stenosis, tennis elbow, dupuytren's contractures, restless leg syndrome, osteoporosis, osteoarthritis, rheumatoid arthritis, autoimmune disease, polymyositis, gout, dementia, Huntington's disease, Alzheimer's disease, brain atrophy, aging-related mobility disability (e.g., frailty), cognitive decline, age related dementia, memory impairment, Lewy body dementia, frontotemporal dementia, Parkinson's disease, mild cognitive impairment, vascular dementia, stroke, transient ischemic attack, trigeminal neuralgia, neuropathy, sleep disorders, insomnia, atherosclerosis, arteriosclerosis, hypertension, heart dysfunction such as cardiac hypertrophy, systolic dysfunction, or diastolic dysfunction, heart failure, dilated cardiomyopathy, heart failure with preserved ejection fraction, arrhythmias, valvular heart disease, chronic obstructive pulmonary disease, chronic obstructive pulmonary disease exacerbations, pulmonary emphysema, idiopathic pulmonary fibrosis, pulmonary hypertension, pulmonary embolism, dyspnea, liver disease including NASH and cirrhosis, gallstones, kidney stones, Barrett's esophagus, hemorrhoids, decubitus ulcers, diverticulitis, constipation, colonic polyps, hemorrhoids, fecal incontinence, cachexia, malabsorption, erectile dysfunction, loss of libido, cataracts, age-related macular degeneration, glaucoma, retinal degeneration, retinal detachment, dry eye, presbyopia, falls, vertigo, benign prostatic hypertrophy, prostate cancer, diminished life expectancy, impaired kidney function, chronic renal failure, acute renal failure, glomerulosclerosis, glomerulosclerosis, nephrosclerosis, dehydration, neurogenic bladder, urinary tract infections, cystitis, urinary incontinence, cancer, obesity, metabolic syndrome, prediabetes, diabetes skin atrophy, skin aging, wrinkles, seborrheic keratosis, actinic keratosis, skin cancer, sun-damaged skin, rosacea, onychomycosis, greying of hair, baldness, age-related hearing loss, tinnitus, loss of smell, periodontal disease, tooth decay, dry mouth, thyroid disease, diseases associated with mitochondrial dysfunction, premature aging syndromes and progerias including Werner's syndrome and Hutchinson Guilford Progeria Syndrome, anemia, folic acid-deficiency anemia, coagulopathy, deep venous thrombosis, cachexia, depression, and diminished life expectancy.

In a twenty-sixth embodiment, the invention is a commercial package comprising RAD001, or a pharmaceutically acceptable salt thereof and instructions for the simultaneous, separate or sequential use with BEZ235, or a pharmaceutically acceptable salt thereof, in the promotion or enhancement of an immune response.

In a twenty-seventh embodiment, the invention is a commercial package comprising RAD001, or a pharmaceutically acceptable salt thereof and instructions for the simultaneous, separate or sequential use with BEZ235, or a pharmaceutically acceptable salt thereof, in the treatment of an age related condition.

The invention claimed is:

1. A method of promoting or enhancing an immune response in a subject, comprising administering to the subject simultaneously, separately, or sequentially, a combination comprising (a) about 0.01-0.2 mg/day of RAD001 or a pharmaceutically acceptable salt thereof, and (b) about 1-20 mg/day of BEZ235, or a pharmaceutically acceptable salt thereof, thereby promoting or enhancing an immune response in the subject.

2. The method of claim 1, wherein the RAD001 is in the neutral form.

3. The method of claim 1, wherein the BEZ235 is in the form of the monotosylate salt.

4. The method of claim 1, wherein the subject is immunocompromised.

5. The method of claim 1, wherein the subject has an impaired immune response.

6. The method of claim 1, wherein the subject is immunoscenescent.

7. The method of claim 1, comprising treating the subject for an age related condition.

8. The method of claim 7, wherein the age related condition is selected from the group consisting of immunosenescence, sarcopenia, muscle wasting, tendon stiffness, tendon injury, tendonitis, Achilles rupture, adhesive capsulitis of shoulder, plantar fasciitis, polymyalgia rheumatica, rotator cuff tear, spinal stenosis, tennis elbow, dupuytren's contractures, restless leg syndrome, osteoporosis, osteoarthritis, rheumatoid arthritis, autoimmune disease, polymyositis, gout, dementia, Huntington's disease, Alzheimer's disease, brain atrophy, aging-related mobility disability, cognitive decline, age related dementia, memory impairment, Lewy body dementia, frontotemporal dementia, Parkinson's disease, mild cognitive impairment, vascular dementia, stroke, transient ischemic attack, trigeminal neuralgia, neuropathy, sleep disorders, insomnia, atherosclerosis, arteriosclerosis, hypertension, heart dysfunction, chronic obstructive pulmonary disease, chronic obstructive pulmonary disease exacerbations, pulmonary emphysema, idiopathic pulmonary fibrosis, pulmonary hypertension, pulmonary embolism, dyspnea, liver disease, gallstones, kidney stones, Barrett's esophagus, hemorrhoids, decubitus ulcers, diverticulitis, constipation, colonic polyps, hemorrhoids, fecal incontinence, cachexia, malabsorption, erectile dysfunction, loss of libido, cataracts, age-related macular degeneration, glaucoma, retinal degeneration, retinal detachment, dry eye, presbyopia, falls, vertigo, benign prostatic hypertrophy, prostate cancer, diminished life expectancy, impaired kidney function, chronic renal failure, acute renal failure, glomerulosclerosis, glomerulosclerosis, nephrosclerosis, dehydration, neurogenic bladder, urinary tract infections, cystitis, urinary incontinence, cancer, obesity, metabolic syndrome, prediabetes, diabetes skin atrophy, skin aging, wrinkles, seborrheic keratosis, actinic keratosis, skin cancer, sun-damaged skin, rosacea, onychomycosis, greying of hair, baldness, age-related hearing loss, tinnitus, loss of smell, periodontal disease, tooth decay, dry mouth, thyroid disease, diseases associated with mitochondrial dysfunction, premature aging syndromes and progerias, anemia, folic acid-deficiency anemia, coagulopathy, deep venous thrombosis, cachexia, depression, and diminished life expectancy.

9. A pharmaceutical composition comprising a combination according to claim 1 and at least one pharmaceutically acceptable carrier.

10. A method of treating a subject having an age related condition which comprises administering to said subject a combination according to claim 1 in a quantity which is jointly therapeutically effective against said age related condition.

11. The method according to claim 10, wherein the age related condition is selected from the group consisting of immunosenescence, sarcopenia, muscle wasting, tendon stiffness, tendon injury, tendonitis, Achilles rupture, adhesive capsulitis of shoulder, plantar fasciitis, polymyalgia rheumatica, rotator cuff tear, spinal stenosis, tennis elbow, dupuytren's contractures, restless leg syndrome, osteoporosis, osteoarthritis, rheumatoid arthritis, autoimmune disease, polymyositis, gout, dementia, Huntington's disease, Alzheimer's disease, brain atrophy, aging-related mobility disability, cognitive decline, age related dementia, memory impairment, Lewy body dementia, frontotemporal dementia, Parkinson's disease, mild cognitive impairment, vascular dementia, stroke, transient ischemic attack, trigeminal neuralgia, neuropathy, sleep disorders, insomnia, atherosclerosis, arteriosclerosis, hypertension, heart dysfunction, chronic obstructive pulmonary disease, chronic obstructive pulmonary disease exacerbations, pulmonary emphysema, idiopathic pulmonary fibrosis, pulmonary hypertension, pulmonary embolism, dyspnea, liver disease, gallstones, kidney stones, Barrett's esophagus, hemorrhoids, decubitus ulcers, diverticulitis, constipation, colonic polyps, hemorrhoids, fecal incontinence, cachexia, malabsorption, erectile dysfunction, loss of libido, cataracts, age-related macular degeneration, glaucoma, retinal degeneration, retinal detachment, dry eye, presbyopia, falls, vertigo, benign prostatic hypertrophy, prostate cancer, diminished life expectancy, impaired kidney function, chronic renal failure, acute renal failure, glomerulosclerosis, glomerulosclerosis, nephrosclerosis, dehydration, neurogenic bladder, urinary tract infections, cystitis, urinary incontinence, cancer, obesity, metabolic syndrome, prediabetes, diabetes skin atrophy, skin aging, wrinkles, seborrheic keratosis, actinic keratosis, skin cancer, sun-damaged skin, rosacea, onychomycosis, greying of hair, baldness, age-related hearing loss, tinnitus, loss of smell, periodontal disease, tooth decay, dry mouth, thyroid disease, diseases associated with mitochondrial dysfunction, premature aging syndromes and progerias, anemia, folic acid-deficiency anemia, coagulopathy, deep venous thrombosis, cachexia, depression, and diminished life expectancy.

12. The method of claim 1, comprising administering about 0.1 mg/day of RAD001 or a pharmaceutically acceptable salt thereof.

13. The method of claim 1, comprising administering about 10 mg/day of BEZ235 or a pharmaceutically acceptable salt thereof.

14. The method of claim 13, wherein the BEZ235 is in the form of the monotosylate salt.

15. The method of claim 1, wherein administration occurs simultaneously.

16. The method of claim 1, wherein administration occurs separately.

17. The method of claim 1, comprising administering about 0.1 mg/day of RAD001 or a pharmaceutically acceptable salt thereof and administering about 10 mg/day of BEZ235 or a pharmaceutically acceptable salt thereof.

18. The method of claim 8, wherein the aging-related mobility disability is frailty.

19. The method of claim 11, wherein the aging-related mobility disability is frailty.

20. The method of claim 8, wherein:

the heart dysfunction is selected from cardiac hypertrophy, systolic dysfunction, or diastolic dysfunction, heart failure, dilated cardiomyopathy, heart failure with preserved ejection fraction, arrhythmias, and valvular heart disease;

the liver disease is selected from NASH and cirrhosis; and the premature aging syndromes and progerias are selected from Werner's syndrome and Hutchinson Guilford Progeria Syndrome.

21. The method of claim 11, wherein:

the heart dysfunction is selected from cardiac hypertrophy, systolic dysfunction, or diastolic dysfunction, heart failure, dilated cardiomyopathy, heart failure with preserved ejection fraction, arrhythmias, and valvular heart disease;

the liver disease is selected from NASH and cirrhosis; and the premature aging syndromes and progerias are selected from Werner's syndrome and Hutchinson Guilford Progeria Syndrome.

\* \* \* \* \*